US010512271B2

(12) United States Patent
Rautenbach et al.

(10) Patent No.: US 10,512,271 B2
(45) Date of Patent: Dec. 24, 2019

(54) METHOD FOR PREVENTING OR TREATING MICROBIAL GROWTH ON A MANUFACTURED PRODUCT

(71) Applicant: Stellenbosch University, Stellenbosch (ZA)

(72) Inventors: Marina Rautenbach, Stellenbosch (ZA); Wilma Van Rensburg, Cape Town (ZA)

(73) Assignee: STELLENBOSCH UNIVERSITY, Western Cape Province (ZA)

( * ) Notice: Subject to any disclaimer, the term of this patent is extended or adjusted under 35 U.S.C. 154(b) by 0 days.

(21) Appl. No.: 15/315,755

(22) PCT Filed: Jun. 2, 2015

(86) PCT No.: PCT/IB2015/054166
§ 371 (c)(1),
(2) Date: Dec. 2, 2016

(87) PCT Pub. No.: WO2015/186058
PCT Pub. Date: Dec. 10, 2015

(65) Prior Publication Data
US 2017/0118994 A1 May 4, 2017

(30) Foreign Application Priority Data

Jun. 3, 2014 (ZA) .................................. 2014/04023

(51) Int. Cl.
| A61L 26/00 | (2006.01) |
| A61L 29/16 | (2006.01) |
| A61L 31/16 | (2006.01) |
| A01N 63/02 | (2006.01) |
| A61L 29/04 | (2006.01) |
| A61L 31/04 | (2006.01) |
| A01N 37/46 | (2006.01) |
| A01N 25/08 | (2006.01) |
| A61L 2/18 | (2006.01) |
| C09D 5/14 | (2006.01) |

(52) U.S. Cl.
CPC ............ *A01N 63/02* (2013.01); *A01N 25/08* (2013.01); *A01N 37/46* (2013.01); *A61L 2/18* (2013.01); *A61L 26/0047* (2013.01); *A61L 26/0066* (2013.01); *A61L 29/048* (2013.01); *A61L 31/047* (2013.01); *A61L 31/16* (2013.01); *C09D 5/14* (2013.01); *A61L 2300/406* (2013.01)

(58) Field of Classification Search
CPC ........ A01N 25/08; A01N 63/02; A61K 38/12; A61L 2/18; A61L 12/14; A61L 15/32; A61L 26/0028; A61L 26/0047; A61L 26/0066; A61L 29/044; A61L 29/048; A61L 31/043; A61L 31/047; A61L 31/10; A61L 31/16; A61L 2300/406; C07K 7/66; C09D 5/14; C09D 5/1637
See application file for complete search history.

(56) References Cited

U.S. PATENT DOCUMENTS

| 2,528,022 A * | 10/1950 | Van Dolah ............. B01J 47/014 536/14 |
| 2,571,849 A * | 10/1951 | Elson ..................... A61L 15/46 424/445 |
| 2,723,217 A * | 11/1955 | Gershon ................. A61K 8/64 424/49 |
| 3,089,818 A * | 5/1963 | Stone ..................... A61K 9/146 252/363.5 |
| 6,630,197 B1 | 10/2003 | Wood |
| 7,781,498 B2 | 8/2010 | Krishnan |
| 10,226,425 B2 * | 3/2019 | Gerashchenko ..... A61K 9/0014 |
| 2003/0176530 A1 * | 9/2003 | Lindley ................ A45C 11/005 523/106 |
| 2015/0030566 A1 | 1/2015 | Rautenbach et al. |
| 2015/0374641 A1 * | 12/2015 | Kim ..................... A61K 31/722 514/2.9 |

FOREIGN PATENT DOCUMENTS

WO 2010/098843 A2 9/2010

OTHER PUBLICATIONS

Loll et al. The high resolution structure of tyrocidine A reveals an amphipathic dimer. Biochimica et Biophysica Acta Biomembranes. Feb. 11, 2014, vol. 1838, pp. 1199-1207.*

Jayaraman et al. (1999) "Inhibiting sulfate-reducing bacteria in biofilms on steel with antimicrobial peptides generated in situ," Appl. Microbiol. Biotechnol. 52:267-275.

Spathelf et al. (2009) "Anti-listerial activity and structure-activity relationships of the six major tyrocidines, cyclic decapeptides from Bacillus aneurinolyticus," Bioorg. Med. Chem. 17(15):5541-5548.

Troskie et al. (Apr. 21, 2014) "Synergistic Activity of the Tyrocidines, Antimicrobial Cyclodecapeptides from Bacillus aneurinolyticus, with Amphotericin B and Caspofungin against Candida albicans Biofilms," Antimicrob. Agents Chemother. 58(7):3697-3707.

(Continued)

*Primary Examiner* — Jeffrey E. Russel
(74) *Attorney, Agent, or Firm* — Brian C. Trinque; Lathrop Gage LLP

(57) ABSTRACT

The invention provides a method for preventing or treating microbial growth on a manufactured material or product. A composition comprising a cyclic decapeptide which is a tyrocidine, trypocidine, phenycidine or gramicidin S having an amino acid sequence of cyclo(valine-$X_1$-leucine-D-phenylalanine-proline-$X_2$-$X_3$-$X_4$-$X_5$-$X_6$) (SEQ ID NO: 1) is applied to the product and the cyclic decapeptides are adsorbed onto the product. Suitable products include medical devices (e.g. a catheter), wound dressings, food packaging, containers, wrappings, surfaces or devices used in the processing, transport or storage of food, filters, composites, paper, wrapping materials, walls, work surfaces, floors, pipes or the like. The composition could be used to disinfect or sterilise a material, surface or product or to inhibit formation of biofilms and/or biofouling on the surface of the product to which it is applied.

14 Claims, 7 Drawing Sheets
Specification includes a Sequence Listing.

(56) References Cited

OTHER PUBLICATIONS

International Search Report with Written Opinion corresponding to International Patent Application No. PCT/IB2015/054166, dated Aug. 12, 2015.

* cited by examiner

METHOD FOR PREVENTING OR TREATING MICROBIAL GROWTH ON A MANUFACTURED PRODUCT

CROSS-REFERENCE TO RELATED APPLICATIONS

This application claims priority to South African provisional patent application number 2014/04023, which is incorporated by reference herein.

SEQUENCE LISTING

This application contains a Sequence Listing in computer readable format. The Sequence Listing is provided as a file entitled 586732_Sequence_Listing.txt created Oct. 16, 2017 which is 44,720 bytes in size. The information in the computer readable format of the Sequence Listing is incorporated herein by reference in its entirety.

FIELD OF THE INVENTION

This invention relates to the adsorption of antimicrobial peptides to solid surfaces or matrixes for inhibiting surface microbial contamination and subsequent biofilm formation on surfaces.

BACKGROUND OF THE INVENTION

Colonisation and adhesion of pathogens to solid surfaces is an ever present problem in agriculture, the food industry, the medical field and various other industries, as this can lead to spoilage of products, fruit and vegetables, chronic infections and/or the formation of antibiotic resistant biofilms.

In agriculture, post-harvest losses are in the region of 24% in the USA (U.S. Dept. of Agriculture, 1965, U.S. Dept. Agr. Hdbk., 291) and about 50% in underdeveloped tropical countries (Courtsey and Booth, 1972, Rev. Plant. Pathol., 51:751-765). Post-harvest spoilage can be prevented by the use of chemical sprays, dips or washes; fumigation; or the use of treated wrappers, box liners or shredded paper. Chemical treatments generally make use of borax, sodium ortho-phenylphenate, chlorine, antibiotics, diphenylamine or ethoxyquin. Sulfur dioxide, nitrogen trichloride, ammonia or ammonium compounds or carbon dioxide are usually used for fumigation. Packaging material is treated with biphenyl, orthophenylphenol, iodine, copper sulphate, mineral oil and diphenylamine. Biphenyl is used in wrappers or box liners, often in conjunction with other treatments such as borax (Godfrey and Ryall, 1948, Texas Agr. Expt Sta. Bul. 701-724; Harvey, 1952, Phytopath., 42: 514). This lowers the occurrence of blue and green molds on citrus and stem-end rots (Harvey and Sinclair, 1953, Rept. Tech. Com. Citrus Assoc. Univ. of Calif., 1-27), but rather than killing fungal infections, the vegetative growth and spore formation of citrus pathogens are merely inhibited. Biphenyl has also been found to stimulate the growth of some vegetable and fruit pathogens (Heiberg and Ramsey, 1946, Pytopath, 36:887-891). Orthophenylphenol-impregnated wrappers have been shown to be effective against some citrus fungi and to lower the infection of tomatoes, grapes and apples (Plank, Rattrey and van Wyk, 1940, Jour. Pomol. And Hort. Sci., 18:135-144). However, injury and scalding of the fruit has been observed after exposure to orthophenylphenol-impregnated wrappers. Iodine-impregnated wrappers have also been shown to have activity against blue mold, without damage to citrus, but iodine's volatile nature causes the inhibitory effect to wear off quickly (Smith, 1962, Botanical Review. 23(3):411-445). Other treatments are also known to prevent fungal infections, but with a range of drawbacks, of which damage to the fruit and vegetables is most prominent. A safe and effective antimicrobial treatment that does not damage fruits and vegetables would therefore be of great use in the agricultural industry.

In the medical field and related industries, the treatment of biofilms is primarily directed at the removal of mature biofilms. Resistance to currently available treatments has been observed and can be due to the exopolysaccharide matrix preventing the penetration of treatments into the entire biofilm, or differences in metabolism between layers of the biofilm and mixed organism biofilms, where not all the organisms are affected by the treatment. It has been found that the most effective way to remove biofilms consists of a combined effort including a treatment and physical removal of the biofilm, e.g. scrubbing or high pressure spraying. This, however, is not possible in all areas where biofilms could form.

Urinary catheters, which are typically made of silicone or latex, are an example in the medical field where biofilm formation is common. A study of catheter biofilms (Stickeler, 1996, Biofouling, 94:293-305) found that in instances where catheters were inserted for longer than 28 days, most patients developed an infection due to a biofilm found in the catheter itself. Commonly found organisms in catheter biofilms are *Staphylococcus epidermis, Enterococcus faecalis, Escherichia coli, Proteus marabilis, Pseudomonas aeruginosa* and *Klebsiella pneumonia*. It has been found that the hydrophobicity of both the organisms and catheter material determines the type of organisms found within the biofilm (Brisset, Vernet-Garnier, Carquin, Burde, Flament and Choisy, 1996, Pathol. Bio., 44:397-404). No specific catheter material has been found to possess the means to prevent colonisation of organisms (Tunney, Jones and Gorman, 1999, Doyle RJ (Eds), Methods in Enzymology. San Diego: Academic Press. 558-566). Control measures such as antimicrobial agents in collection bags, antimicrobial ointments and lubricants, the use of antibiotics and bladder installation and irrigation have been tested, but none of these showed significant results (Kaye and Hessen, 1994, IN: Bisno and Waldovogel (Eds), Infection associated with indwelling medical devices. Washington. American Society for Microbiology, 291-307). Only silver-impregnated catheter tubes, which delayed the attachment of organisms for 4 days, showed an improvement.

Wound dressings are another example within the medical field where surface contamination is problematic, often leading to infection of the wounds which the dressings are supposed to protect. Impregnated wound dressings with bactericidal, virocidal or fungicidal activity have been developed for use on wounds that are already infected, i.e. to not only aid the healing of the wound, but to also fight the infection that is preventing the healing of the wound. For example, Betadine™ wound dressing is impregnated with 10% povidone-iodine solution, has bactericidal and virucidal activity and is marketed for use on contaminated or superficially infected wounds (Herruzo-Cabiera, Vizcaino-Alcaide, Mayer, Rey-Calero, 1992, Burns, 18:35-37). A drawback of this dressing, however, is that it becomes stiff as it dries, which can cause discomfort to the patient and can also disrupt the wound. Silver impregnated dressings are also used to fight infected wounds, such as Acticoat™ (Westaim Biomedical Inc., Fort. Saskatchewan, Alberta, Canada) and SilverIon® (Argentum Medical, L.L.C., Lakermont, Ga.). Both of these dressings use nanocrystalline silver to release silver to the wound area in a controlled and prolonged manner, resulting in a lower frequency of changing of the dressing, lower risk of further infection, lower cost of treatment and preventing continuous patient discomfort and tissue damage. However, few studies have been conducted on the effect of silver on the wound bed, how it is metabolised or how it effects the overall healing process of the wound.

In the food industry, *Listeria monocytogenes* is commonly associated with biofouling and is found in meat and dairy processing plants. Although the sheer force used to clean pipes within the processing plants should be enough to remove exposed biofilms, it is the hard-to-reach places (such as cracks within equipment caused by age, gaskets, valves and joints) that are more likely to develop biofilms and these are difficult to remove. Furthermore, environmental surfaces (floors, walls and the like) have been found to be susceptible to extensive biofilm formation and can lead to the reintroduction of *Listeria* in a cleaned processing plant. In conjunction, resistance of *Listeria* to sanitizing agents used within the food processing environment has been observed. This is of great concern, since *Listeria* is responsible for 28% of deaths caused by the intake of contaminated food in the USA (Mead, Slutsker, Dietz, McCraig, Bresee, Shapiro, Griffin, Tauxe, 1999, Emerg. Infect. Dis. 5: 607-625).

One of the biggest problems with biofouling is that once an organism has adhered and colonised to a surface, it can form resistant biofilms that are difficult to remove completely, leaving a constant source for re-infection or chronic biofouling.

There is thus a need for new ways of preventing or treating microbial infections and biofilm production on surfaces, especially in the agricultural, food and medical industries or, in other industries that encounter instances of infections and/or biofouling.

SUMMARY OF THE INVENTION

According to a first embodiment of the invention, there is provided a method for preventing or treating microbial growth on a manufactured product, the method comprising the step of applying to a surface of the product a composition comprising as active agent a cyclic decapeptide which is a tyrocidine, trypocidine, phenycidine or gramicidin S, or a derivative or analogue thereof, the cyclic decapeptide comprising an amino acid sequence of cyclo(Val-$X_1$-Leu-D-Phe-Pro-$X_2$-$X_3$-$X_4$-$X_5$-$X_6$) (SEQ ID NO: 1), where
  $X_1$ is Orn or Lys;
  $X_2$ is Val, Leu, Ile, Phe, Trp or Tyr;
  $X_3$ is the D-isomer of Val, Leu, Ile, Phe, Trp, Tyr, Orn or Lys;
  $X_4$ is Asn, Gln or Leu;
  $X_5$ is Gln, the D-isomer of Val, Leu or Ile; and
  $X_6$ is Tyr, Phe, Trp, Pro or Hyp.

In one embodiment, the cyclic decapeptide may be a tyrocidine with the sequence cyclo(Val-$X_1$-Leu-D-Phe-Pro-$X_7$-$X_8$-Asn-Gln-$X_9$) (SEQ ID NO: 2) or an analogue or derivative thereof, where:
  $X_1$ is Orn or Lys;
  $X_7$ is Trp or Phe;
  $X_8$ is D-Trp or D-Phe; and
  $X_9$ is Tyr, Trp or Phe.

The cyclic decapeptide may be gramicidin S or a derivative or analogue thereof, with the amino acid sequence of cyclo(Val-$X_1$-Leu-D-Phe-Pro-Val-$X_1$-Leu-D-Phe-Pro) (SEQ ID NO: 3).

The cyclic decapeptide may also be a derivative or analogue of a tyrocidine, tryptocidine, phenycidine or gramicidin S, and may have one or more of the following amino acid substitutions:
  the valine residue may be substituted with a leucine or isoleucine residue;
  the leucine residue may be substituted with an isoleucine or valine residue;
  the phenylalanine residue may be substituted with a tryptophan or tyrosine residue;
  the proline residue may be substituted with a hydroxyproline residue; or
  the ornithine residue may be substituted with a lysine or cationic amino acid; or
  an analogue or derivative thereof.

For example, the cyclic decapeptide may have an amino acid sequence selected from any one of SEQ ID NOS: 6-177.

The composition may contain a mixture of any two or more different cyclic decapeptides with an amino acid sequence of SEQ ID NO: 1.

The product may be made from or derived from a polymer, such as a natural, synthetic or semi-synthetic polymer or a combination thereof.

Suitable natural polymers include sugar-polymers (i.e. paper and paper products, chitin, starch, cotton and the like), leather, latex, glass, rubber, silk or any other derived solid or solidified material which is susceptible to microbial contamination.

The product may be a medical device or part thereof, a wound dressing or part thereof, food packaging, a container, wrapping, a surface or device used in the processing, transport or storage of food, a filter, a composite, paper, wrapping material, a container or the like.

The microbial growth to be prevented or treated may be fungal and/or bacterial growth.

The composition may be applied to the manufactured product in a liquid form, gel, aerosol or mist or during preparation of the product so that the cyclic decapeptides can adsorb onto or into the surface of the product or onto or into the polymers from which the product is made.

According to a second embodiment of the invention, there is provided a manufactured product onto which an antimicrobial composition has been applied according to the method described above.

DETAILED DESCRIPTION OF THE INVENTION

Figure 1:
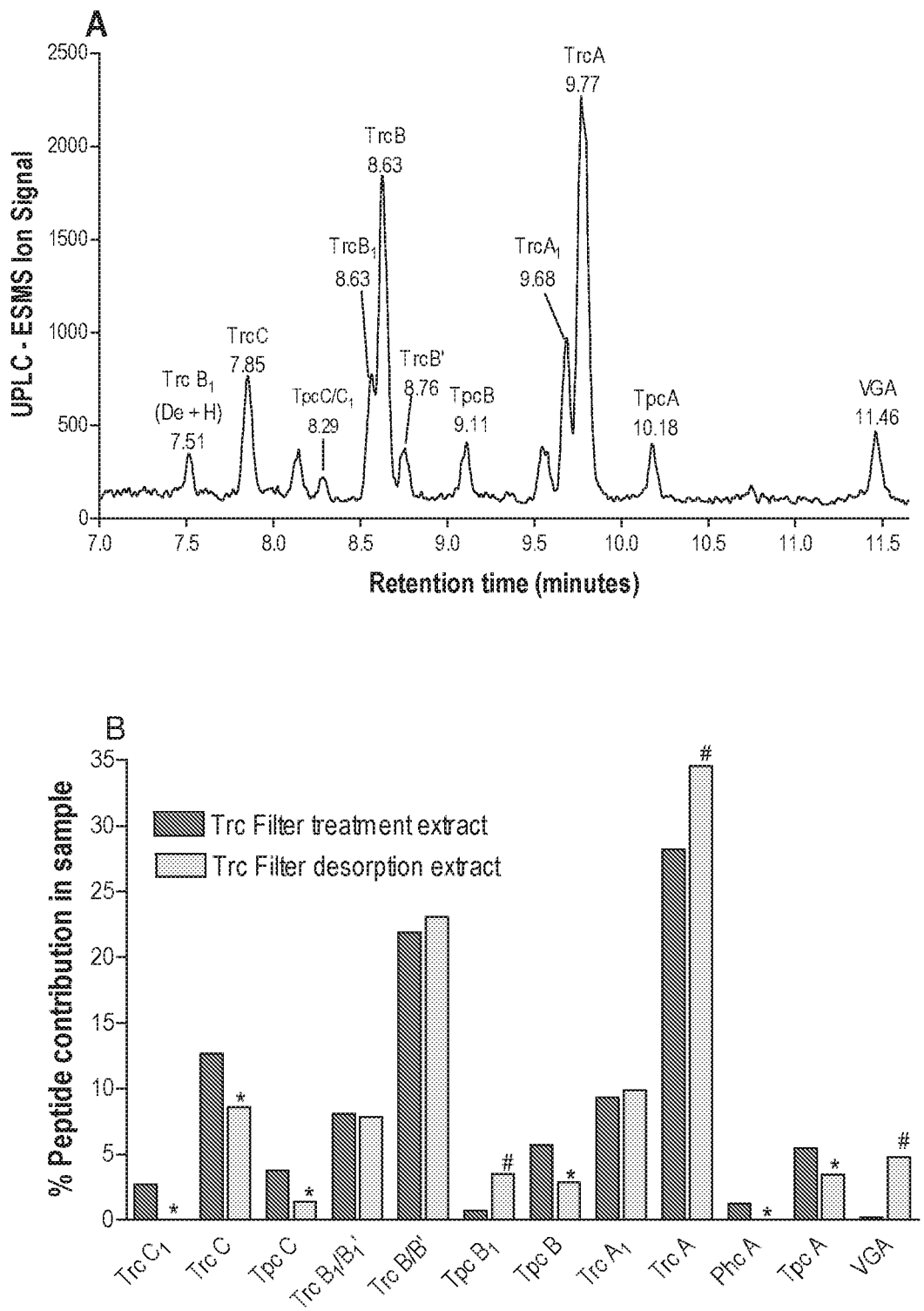
FIG. 1: UPLC-ESMS profile of a tyrocidine (Trc) extract desorbed from Trc treated cellulose (CL) filters. The identity of the peptides is indicated (A). Comparison of the contribution of the different peptides in the Trc mixture desorbed from the CL filter compared to peptides in the Trc extract used for the CL filter treatment. Peptide contribution denoted with * decreased and those with # increased contribution compared to the treatment extract (B).

A method for preventing or treating microbial growth on a manufactured material or product, or for inactivating or killing microbes thereon, is described herein. The method comprises the step of applying to the surface of the manufactured material or product a composition comprising as an active agent a cyclic decapeptide which is a tyrocidine, trypocidine, phenycidine or gramicidin S, or a derivative or analogue thereof, the cyclic decapeptide comprising an amino acid sequence of cyclo(valine-$X_1$-leucine-D-phenylalanine-proline-$X_2$—$X_3$-$X_4$-$X_5$-$X_6$) (SEQ ID NO: 1).

The manufactured product can be a material which can be used to produce another product or can be an end-product itself. The manufactured product is preferably made from or derived from a polymer. Suitable natural polymers include sugar-polymers (e.g. paper, tissue paper, cardboard, wood, polymers from modified cellulose, chitin, chitosan, starch, cotton etc.), leather, latex, glass, rubber, silk or any other derived solid or solidified material which is susceptible to microbial contamination. Suitable synthetic or semi-synthetic polymers include polyvinylidene (i.e. containing fluoride, iodine, bromide or chloride), polyvinyl, polyester, polystyrene, polyethylene/polypropylene and the like, polyurethane, polyacrylamide, polyamide/imide and the like (nylons), polyepoxide (epoxies), polyether-ether ketone (PEEK), polyetherimide, polylactic acid and the like, polymethyl acrylate and the like (acrylates), polytetrafluoroethylene and the like (teflons), polyfurfuryl alcohol, polysulfone, polycarbonate, ureaformaldehyde, polymers from modified cellulose (e.g. nitrocellulose, cellulose acetate and the like), acrylics, polymaleimide and the like, melamine, silicone or any other synthetically derived organic polymer, solid or solidified material which is susceptible to microbial contamination, including synthetic polymeric materials made from nanofibres. The manufactured material may also be a product made from a mixture of natural, synthetic and/or semi-synthetic polymers.

The product may have at least one solid or matrix-like surface.

The manufactured material is not a botanical plant or an unprocessed part of a plant, such as a fruit.

The manufactured product can be a medical device or part thereof (e.g. a catheter), a wound dressing or part thereof, food packaging, a container, wrapping, a surface or device used in the processing, transport or storage of food, a filter, a composite, paper, wrapping material, a wall, a work surface, a floor, a pipe or the like.

When applied to the surface of the material or product, the cyclic decapeptides will adsorb to the surface or become impregnated therein, and will prevent or inhibit attachment of microbes (such as from fungi, bacteria or other microorganisms) to the surface. The composition could also be used to inactivate or kill microorganisms, thus preventing the spread of microbial pathogens ("germs"). Thus, it is envisaged that the composition could be used to disinfect or sterilise a material, surface or product. The composition could also be used to inhibit formation of biofilms and/or biofouling on the surface of the product to which it is applied.

As used herein, a biofilm is a thin microbial layer, containing mostly biocide- or antibiotic-resistant microorganisms (such as bacteria and/or fungi), that forms on and coats various surfaces (such as catheters or water pipes).

Biofouling is the gradual accumulation of organisms (such as bacteria and protozoa, and in particular those that are waterborne) on the surfaces of structures that contributes to corrosion of the structures and to a decrease in the efficiency of moving parts. The structures are typically structures which are exposed to water or aqueous media.

Disinfection is the cleaning of something, especially by using a substance that kills microbes ("germs") such as bacteria and fungi.

Sterilization is a term referring to any process that eliminates or kills all forms of life, including transmissible agents present on a surface, contained in a fluid, in medication, or in a compound such as biological culture media.

The composition may contain two or more different cyclic decapeptides of SEQ ID NO: 1. For example, the composition could include a combination of one or more tyrocidines and/or gramicidin S, or derivatives thereof.

The composition will be formulated to contain a concentration of the cyclic decapeptide(s) which is effective to prevent or inhibit attachment of the microbes to the surface to which the composition is applied or to inactivate or kill microbes which come into contact with the surface.

The composition can be applied to the surface of the manufactured material in a liquid or semi-liquid form so that the cyclic decapeptides can adsorb onto the surface of the material or product. For example, the composition can be in a liquid, gel, mist, aerosol or any other suitable formulation. Once applied, the composition can be allowed to dry. Alternatively, once the cyclic decapeptides have been able to adsorb to the surface of the product, a washing step may be performed to remove excess peptides which have not adsorbed to the product.

The composition can be suitably formulated to improve solid phase adhesion to the manufactured material, to improve activity or stability of the cyclic decapeptides, or to limit toxicity thereof.

As the peptides are adsorbed to the surface of the product rather than being covalently bound thereto, they are able to release from the surface when a target microorganism is present and will instead bind to the microorganism, thereby preventing the microorganism from adhering to the product. Thus, the composition will act in a slow-release manner, and the peptides can provide anti-microbial activity to the surface of the product over a sustained period of time.

Gramicidin S, tyrocidines, tryptocidines and phenycidines and derivatives/analogues thereof are broad spectrum microbiocides that are active against both bacterial and fungal contamination. The cyclic decapeptides analogues to the tyrocidines also show low phytotoxicity. The cyclic decapeptides described herein are heat stable, work over a wide pH range and are relatively insensitive to mineral salts. Moreover, because they are cyclic, they are less likely to be rapidly degraded like linear peptides. It is therefore envisaged that the compositions of the invention will be suitable for offering long term antimicrobial protection on manufactured surfaces.

Tyrocidines, tryptocidines, phenycidines and/or gramicidin S are β-sheet cyclic decapeptide family produced by *Bacillus* (e.g. *Bacillus* aneurinolyticus) and *Brevibacillus* (*Bacillus brevis*) spp., respectively. These peptides have high sequence identity, are highly conserved and adopt a similar backbone conformation/molecular topology. Tyrocidines and gramicidin S have a common sequence of Val-Orn-Leu-D-Phe-Pro (SEQ ID NO: 4), where the cationic residue can either be ornithine or lysine. The valine and leucine residues can also be substituted for leucine, isoleucine and valine for tyrocidines. The complete gramicidin S sequence is a repeat of the highly conserved sequence of cyclo(Val-Orn-Leu-D-Phe-Pro)$_2$ (SEQ ID NO: 3). The complete tyrocidine sequence also contains this highly conserved sequence, but instead of a repeat thereof it is followed by a variable pentapeptide moiety, Phe-D-Phe-Asn-Gln-Tyr (SEQ ID NO: 5) or a derivative or analogue thereof. Any one or more of the three aromatic residues in the variable peptide moiety can be substituted with tyrosine, phenylalanine or tryptophan, giving rise to tyrocidines, phenycidines and tryptocidines.

The primary chemical structures of gramicidin S and tyrocidine A (one of the tyrocidines) are shown below:

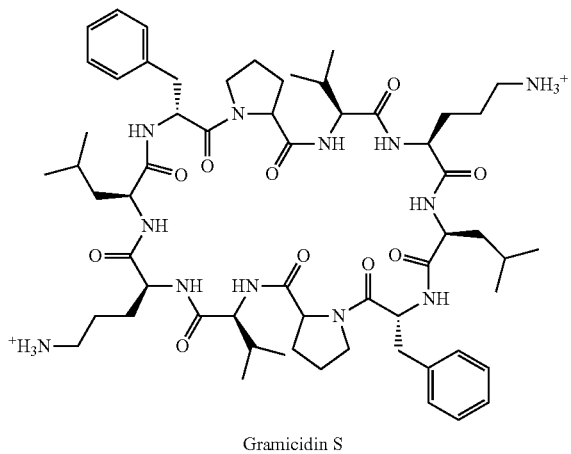

Gramicidin S

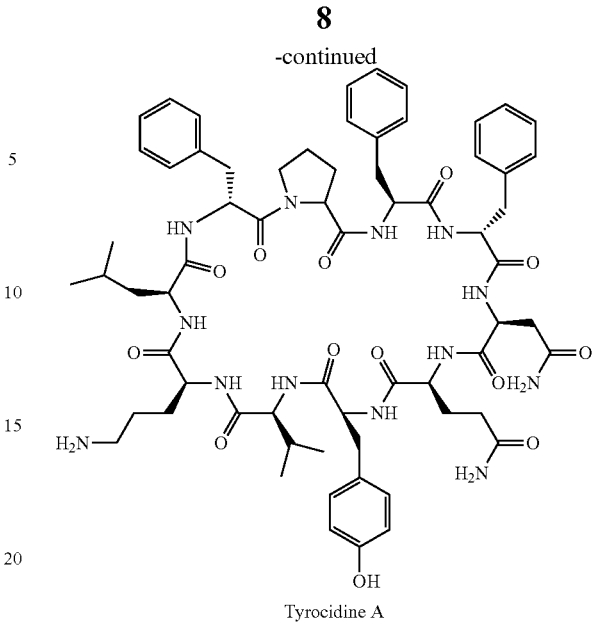

Tyrocidine A

Tyrothricin (a tyrocidine-gramicidin complex where the gramicidins are linear neutral 15-mer peptides not related to gramicidin S) was the first antibiotic to be used in clinical practices, but later fell into disrepute due to its haemolytic toxicity (Dubos and Cattaneo, 1939, J. Exp. Med. 70: 249; Hotchkiss and Dubos, 1941, J. Biol. Chem., 141: 155; Bradshaw, 2003, Biodrugs, 17: 233-240). Studies have shown that tyrocidines have activity against *Neurospora crassa* (Mach and Slayman, 1966, BBA, 124: 351-336) and Gram-positive bacteria such as *Listeria monocytogenes* (Spathelf and Rautenbach, 2009, Bioorg. Med. Chem, 17: 5541-5548), with the tyrocidines preventing *L. monocytogenes* biofilm formation (personal communication, A. N.-N. Leussa). Tyrothricin and the tyrocidines are also active against *Candida albicans* (Kretschmar et. al., 1996, Mysoses, 39: 45-50) and *C. albicans* biofilms (Troskie et al, 2014, Antimicrob. Agents Chemother, 58, 3697-3707). The applicant is, however, not aware of any studies which have been conducted on tyrothricin producers (e.g. *Bacillus aneurinolyticus*, commonly referred to as the Dubos strain of *Bacillus brevis*) or tyrocidines in sterilisation and the control of cell attachment to solid surfaces or matrixes or biofilm/biofouling prevention. This is possibly due to the perceived high toxicity of these peptides, although it would appear that this perception is unfounded (Rautenbach et. al., 2007, BBA Biomembr., 1768: 1488-1497). The tyrothricin complex has also been used in throat lozenges (1 mg tyrothricin per lozenge) under the trade name Tyrozets, indicating its relative safety for human consumption, although this product has been discontinued due to questionable efficacy. This complex has also been used in other studies as a gel, under the trade names Tyrosur® and Limex®, and has been shown to not have a curative effect on superficial wounds compared to the vehicle (gel without tyrothricin) and the untreated wound areas (Wigger-Alberti et. al., 2013, Skin Pharmacol Physiol, 26: 52-56).

The cyclic decapeptides of the present invention are known tyrocidines, tryptocidines, phenycidines or gramicidin S, or derivatives or analogues thereof, which have a highly conserved amino acid sequence comprising Val-$X_1$-Leu-D-Phe-Pro-$X_2$-$X_3$-$X_4$-$X_5$-$X_6$ (SEQ ID NO: 1), where $X_1$ is ornithine or lysine, or a derivative or analogue thereof.

Suitable analogues of the tyrocidines, tryptocidines, phenycidines or gramicidin S may be those including any one or more of the following substitutions:
- the valine residue substituted with a leucine or isoleucine residue or hydrophobic amino acid or analogue/derivative;
- the leucine residue substituted with an isoleucine or valine residue or hydrophobic amino acid or analogue/derivative;
- the proline residue being replaced by hydroxyproline residue or analogue/derivative thereof;
- the phenylalanine residue substituted with a tryptophan or tyrosine residue or aromatic analogue/derivative thereof;
- the ornithine residue substituted with a lysine or a cationic amino acid or an analogue/derivative thereof;
- $X_2$ being valine, leucine, isoleucine, phenylalanine, tryptophan or tyrosine or a hydrophobic amino acid or analogue/derivative;
- $X_3$ being D-isomer of valine, leucine, isoleucine, phenylalanine, tryptophan or tyrosine or a hydrophobic amino acid or analogue/derivative thereof; or alternatively being an ornithine, lysine or cationic amino acid or analogue/derivative thereof;
- $X_4$ being asparagine, glutamine or leucine or an analogue or derivative thereof;
- $X_5$ being glutamine or a polar amino acid or analogue/derivative thereof; or alternatively being the D-isomer of valine, leucine, isoleucine or a hydrophobic amino acid or analogue/derivative thereof; and
- $X_6$ being a tyrosine, phenylalanine or tryptophan or proline residue.

More preferably, the cyclic decapeptide derivatives may be one or more of the peptides selected from the group consisting of:

```
Tyrocidine analogues:
                                          (SEQ ID NO: 6)
Cyclo-(VKLfPWwNQY) (Tyrocidine C₁, TrcC¹)

(SEQ ID NO: 7)
Cyclo-(VOLfPWwNQY) (Tyrocidine C, TrcC)

(SEQ ID NO: 8)
Cyclo-(VKLfPWfNQY) (Tyrocidine B₁, TrcB₁)

(SEQ ID NO: 9)
Cyclo-(VOLfPWfNQY) (Tyrocidine B, TrcB)

(SEQ ID NO: 10)
Cyclo-(VKLfPFwNQY) (Tyrocidine B₁', TrcB₁')

(SEQ ID NO: 11)
Cyclo-(VOLfPFwNQY) (Tyrocidine B', TrcB')

(SEQ ID NO: 12)
Cyclo-(VKLfPFfNQY) (Tyrocidine A₁, TrcA₁)

(SEQ ID NO: 13)
Cyclo-(VOLfPFfNQY) (Tyrocidine A, TrcA)

(SEQ ID NO: 14)
Cyclo-(VKLfPYwNQY)

(SEQ ID NO: 15)
Cyclo-(VOLfPYwNQY)

(SEQ ID NO: 16)
Cyclo-(VKLfPYfNQY)

(SEQ ID NO: 17)
Cyclo-(VOLfPYfNQY)

(SEQ ID NO: 18)
Cyclo-(VKLfPFyNQY)

(SEQ ID NO: 19)
Cyclo-(VOLfPFyNQY)

(SEQ ID NO: 20)
Cyclo-(VKLfPWyNQY)

(SEQ ID NO: 21)
Cyclo-(VOLfPWyNQY)

(SEQ ID NO: 22)
Cyclo-(LKLfPWwNQY)

(SEQ ID NO: 23)
Cyclo-(LOLfPWwNQY)

(SEQ ID NO: 24)
Cyclo-(LKLfPWfNQY)

(SEQ ID NO: 25)
Cyclo-(LOLfPWfNQY)

(SEQ ID NO: 26)
Cyclo-(LKLfPFwNQY)

(SEQ ID NO: 27)
Cyclo-(LOLfPFwNQY)

(SEQ ID NO: 28)
Cyclo-(LKLfPFfNQY)

(SEQ ID NO: 29)
Cyclo-(LOLfPFfNQY)

(SEQ ID NO: 30)
Cyclo-(LKLfPYwNQY)

(SEQ ID NO: 31)
Cyclo-(LOLfPYwNQY)

(SEQ ID NO: 32)
Cyclo-(LKLfPYfNQY)

(SEQ ID NO: 33)
Cyclo-(LOLfPYfNQY)

(SEQ ID NO: 34)
Cyclo-(LKLfPFyNQY)

(SEQ ID NO: 35)
Cyclo-(LOLfPFyNQY)

(SEQ ID NO: 36)
Cyclo-(LKLfPWyNQY)

(SEQ ID NO: 37)
Cyclo-(LOLfPWyNQY)

(SEQ ID NO: 38)
Cyclo-(IKLfPWwNQY)

(SEQ ID NO: 39)
Cyclo-(IOLfPWwNQY)

(SEQ ID NO: 40)
Cyclo-(IKLfPWfNQY)

(SEQ ID NO: 41)
Cyclo-(IOLfPWfNQY)

(SEQ ID NO: 42)
Cyclo-(IKLfPFwNQY)

(SEQ ID NO: 43)
Cyclo-(IOLfPFwNQY)

(SEQ ID NO: 44)
Cyclo-(IKLfPFfNQY)
```

-continued

Cyclo-(IOLfPFfNQY) (SEQ ID NO: 45)

Cyclo-(IKLfPYwNQY) (SEQ ID NO: 46)

Cyclo-(IOLfPYwNQY) (SEQ ID NO: 47)

Cyclo-(IKLfPYfNQY) (SEQ ID NO: 48)

Cyclo-(IOLfPYfNQY) (SEQ ID NO: 49)

Cyclo-(IKLfPFyNQY) (SEQ ID NO: 50)

Cyclo-(IOLfPFyNQY) (SEQ ID NO: 51)

Cyclo-(IKLfPWyNQY) (SEQ ID NO: 52)

Cyclo-(IOLfPWyNQY) (SEQ ID NO: 53)

Cyclo-(VKLfPLwNQY) (SEQ ID NO: 54)

Cyclo-(VOLfPLwNQY) (SEQ ID NO: 55)

Cyclo-(VKLfPLfNQY) (SEQ ID NO: 56)

Cyclo-(VOLfPLfNQY) (SEQ ID NO: 57)

Cyclo-(VKLfPLyNQY) (SEQ ID NO: 58)

Cyclo-(VOLfPLyNQY) (SEQ ID NO: 59)

Tryptocidine analogues:

Cyclo-(VKLfPWwNQW) (Tryptocidine $C_1$, $TpcC_1$) (SEQ ID NO: 60)

Cyclo-(VOLfPWwNQW) (Tryptocidine C, TpcC) (SEQ ID NO: 61)

Cyclo-(VKLfPWfNQW) (Tryptocidine $B_1$, $TpcB_1$) (SEQ ID NO: 62)

Cyclo-(VOLfPWfNQW) (Tryptocidine B, TpcB) (SEQ ID NO: 63)

Cyclo-(VKLfPFwNQW) (Tryptocidine $B_1$', $TpcB_1$') (SEQ ID NO: 64)

Cyclo-(VOLfPFwNQW) (Tryptocidine B', Tpc6') (SEQ ID NO: 65)

Cyclo-(VKLfPFfNQW) (Tryptocidine $A_1$, $TpcA_1$) (SEQ ID NO: 66)

Cyclo-(VOLfPFfNQW) (Tryptocidine A, TpcA) (SEQ ID NO: 67)

Cyclo-(VKLfPYwNQW) (SEQ ID NO: 68)

Cyclo-(VOLfPYwNQW) (SEQ ID NO: 69)

Cyclo-(VKLfPYfNQW) (SEQ ID NO: 70)

Cyclo-(VOLfPYfNQW) (SEQ ID NO: 71)

Cyclo-(VKLfPFyNQW) (SEQ ID NO: 72)

Cyclo-(VOLfPFyNQW) (SEQ ID NO: 73)

Cyclo-(VKLfPWyNQW) (SEQ ID NO: 74)

Cyclo-(VOLfPWyNQW) (SEQ ID NO: 75)

Cyclo-(LKLfPWwNQW) (SEQ ID NO: 76)

Cyclo-(LOLfPWwNQW) (SEQ ID NO: 77)

Cyclo-(LKLfPWfNQW) (SEQ ID NO: 78)

Cyclo-(LOLfPWfNQW) (SEQ ID NO: 79)

Cyclo-(LKLfPFwNQW) (SEQ ID NO: 80)

Cyclo-(LOLfPFwNQW) (SEQ ID NO: 81)

Cyclo-(LKLfPFfNQW) (SEQ ID NO: 82)

Cyclo-(LOLfPFfNQW) (SEQ ID NO: 83)

Cyclo-(LKLfPYwNQW) (SEQ ID NO: 84)

Cyclo-(LOLfPYwNQW) (SEQ ID NO: 85)

Cyclo-(LKLfPYfNQW) (SEQ ID NO: 86)

Cyclo-(LOLfPYfNQW) (SEQ ID NO: 87)

Cyclo-(LKLfPFyNQW) (SEQ ID NO: 88)

Cyclo-(LOLfPFyNQW) (SEQ ID NO: 89)

Cyclo-(LKLfPWyNQW) (SEQ ID NO: 90)

Cyclo-(LOLfPWyNQW) (SEQ ID NO: 91)

Cyclo-(IKLfPWwNQW) (SEQ ID NO: 92)

Cyclo-(IOLfPWwNQW) (SEQ ID NO: 93)

Cyclo-(IKLfP(WONQW) (SEQ ID NO: 94)

Cyclo-(IOLfP(Wf)NQW) (SEQ ID NO: 95)

Cyclo-(IKLfP(Fw)NQW) (SEQ ID NO: 96)

Cyclo-(IOLfP(Fw)NQW) (SEQ ID NO: 97)

-continued

Cyclo-(IKLfPFfNQW) (SEQ ID NO: 98)

Cyclo-(IOLfPFfNQW) (SEQ ID NO: 99)

Cyclo-(IKLfPYwNQW) (SEQ ID NO: 100)

Cyclo-(IOLfPYwNQW) (SEQ ID NO: 101)

Cyclo-(IKLfPYfNQW) (SEQ ID NO: 102)

Cyclo-(IOLfPYfNQW) (SEQ ID NO: 103)

Cyclo-(IKLfPFyNQW) (SEQ ID NO: 104)

Cyclo-(IOLfPFyNQW) (SEQ ID NO: 105)

Cyclo-(IKLfPWyNQW) (SEQ ID NO: 106)

Cyclo-(IOLfPWyNQW) (SEQ ID NO: 107)

Cyclo-(VKLfPLwNQW) (SEQ ID NO: 108)

Cyclo-(VOLfPLwNQW) (SEQ ID NO: 109)

Cyclo-(VKLfPLfNQW) (SEQ ID NO: 110)

Cyclo-(VOLfPLfNQW) (SEQ ID NO: 111)

Cyclo-(VKLfPLyNQW) (SEQ ID NO: 112)

Cyclo-(VOLfPLyNQW) (SEQ ID NO: 113)

Phenycidine analogues:

Cyclo-(VKLfPWwNQF) (Phenycidine C$_1$, PhcC$_1$) (SEQ ID NO: 114)

Cyclo-(VOLfPWwNQF) (Phenycidine C, PhcC) (SEQ ID NO: 115)

Cyclo-(VKLfPWfNQF) (Phenycidine B$_1$, PhcB$_1$) (SEQ ID NO: 116)

Cyclo-(VOLfPWfNQF) (Phenycidine B, PhcB) (SEQ ID NO: 117)

Cyclo-(VKLfPFwNQF) (Phenycidine B$_1$', PhcB$_1$') (SEQ ID NO: 118)

Cyclo-(VOLfPFwNQF) (Phenycidine B', PhcB') (SEQ ID NO: 119)

Cyclo-(VKLfPFfNQF) (Phenycidine A$_1$, PhcA$_1$) (SEQ ID NO: 120)

Cyclo-(VOLfPFfNQF) (Phenycidine A or Tyrocidine E, PhcA) (SEQ ID NO: 121)

Cyclo-(VKLfPYwNQF) (SEQ ID NO: 122)

Cyclo-(VOLfPYwNQF) (SEQ ID NO: 123)

Cyclo-(VKLfPYfNQF) (SEQ ID NO: 124)

Cyclo-(VOLfPYfNQF) (SEQ ID NO: 125)

Cyclo-(VKLfPFyNQF) (SEQ ID NO: 126)

Cyclo-(VOLfPFyNQF) (SEQ ID NO: 127)

Cyclo-(VKLfPWyNQF) (SEQ ID NO: 128)

Cyclo-(VOLfPWyNQF) (SEQ ID NO: 129)

Cyclo-(LKLfPWwNQF) (SEQ ID NO: 130)

Cyclo-(LOLfPWwNQF) (SEQ ID NO: 131)

Cyclo-(LKLfPWfNQF) (SEQ ID NO: 132)

Cyclo-(LOLfPWfNQF) (SEQ ID NO: 133)

Cyclo-(LKLfPFwNQF) (SEQ ID NO: 134)

Cyclo-(LOLfPFwNQF) (SEQ ID NO: 135)

Cyclo-(LKLfPYwNQF) (SEQ ID NO: 136)

Cyclo-(LOLfPYwNQF) (SEQ ID NO: 137)

Cyclo-(LKLfPYfNQF) (SEQ ID NO: 138)

Cyclo-(LOLfPYfNQF) (SEQ ID NO: 139)

Cyclo-(LKLfPFyNQF) (SEQ ID NO: 140)

Cyclo-(LOLfPFyNQF) (SEQ ID NO: 141)

Cyclo-(LKLfPWyNQF) (SEQ ID NO: 142)

Cyclo-(LOLfPWyNQF) (SEQ ID NO: 143)

Cyclo-(LKLfPFfNQF) (SEQ ID NO: 144)

Cyclo-(LOLfPFfNQF) (SEQ ID NO: 145)

Cyclo-(IKLfPWwNQF) (SEQ ID NO: 146)

Cyclo-(IOLfPWwNQF) (SEQ ID NO: 147)

Cyclo-(IKLfPWfNQF) (SEQ ID NO: 148)

Cyclo-(IOLfPWfNQF) (SEQ ID NO: 149)

Cyclo-(IKLfPFwNQF) (SEQ ID NO: 150)

```
Cyclo-(IOLfPFwNQF)              (SEQ ID NO: 151)

Cyclo-(IKLfPYwNQF)              (SEQ ID NO: 152)

Cyclo-(IOLfPYwNQF)              (SEQ ID NO: 153)

Cyclo-(IKLfPYfNQF)              (SEQ ID NO: 154)

Cyclo-(IOLfPYfNQF)              (SEQ ID NO: 155)

Cyclo-(IKLfPFyNQF)              (SEQ ID NO: 156)

Cyclo-(IOLfPFyNQF)              (SEQ ID NO: 157)

Cyclo-(IKLfPWyNQF)              (SEQ ID NO: 158)

Cyclo-(IOLfPWyNQF)              (SEQ ID NO: 159)

Cyclo-(IKLfPFfNQF)              (SEQ ID NO: 160)

Cyclo-(IOLfPFfNQF)              (SEQ ID NO: 161)

Cyclo-(VKLfPLwNQF)              (SEQ ID NO: 162)

Cyclo-(VOLfPLwNQF)              (SEQ ID NO: 163)

Cyclo-(VKLfPLfNQF)              (SEQ ID NO: 164)

Cyclo-(VOLfPLfNQF)              (SEQ ID NO: 165)

Cyclo-(VKLfPLyNQF)              (SEQ ID NO: 166)

Cyclo-(VOLfPLyNQF)              (SEQ ID NO: 167)

Gramicidin S analogues:
Cyclo-(VOLfPVOLfP) (Gramicidin S)    (SEQ ID NO: 168)

Cyclo-(VKLfPVOLfP)              (SEQ ID NO: 169)

Cyclo-(VKLfPVKLfP)              (SEQ ID NO: 170)

Cyclo-(LOLfPVOLfP)              (SEQ ID NO: 171)

Cyclo-(LKLfPVOLfP)              (SEQ ID NO: 172)

Cyclo-(LOLfPVKLfP)              (SEQ ID NO: 173)

Cyclo-(LKLfPVKLfP)              (SEQ ID NO: 174)

Cyclo-(LOLfPLOLfP)              (SEQ ID NO: 175)

Cyclo-(LKLfPLOLfP)              (SEQ ID NO: 176)

Cyclo-(LKLfPLKLfP)              (SEQ ID NO: 177)
```

In the sequences above, standard upper case abbreviations denote L-amino acids, with the exception of O for ornithine, lower case abbreviations denote a D-residue and cyclo indicates amino to carboxy-terminal cyclisation via an amide bond.

References herein to "cyclic decapeptides" refer to the sequences stated above and analogues or derivatives thereof.

The cyclic decapeptides can be produced by their natural bacterial producers, by genetically modifying a suitable microorganism or by using an organic/semi-synthetic system. The amino acid residues in the derivatives or analogues can separately or in combination be replaced in the core cyclic decapeptide sequence (cyclo(valine-ornithine-leucine-D-phenylalanine-proline-$X_2$-$X_3$-$X_4$-$X_5$-$X_6$) (SEQ ID NO: 1) by bacterial/microbial production or using organic/semi-synthetic systems.

The cyclic decapeptides can be chemically or enzymatically modified to improve matrix adhesion and/or solubility and/or bio-activity and/or to limit toxicity. Modification methods include activation for covalent coupling, oxidation, hydroxylation, acylation, amidation, coupling of an organic moiety, hydroxyl, carboxyl, carbonyl, amino, methyl or sugar/sugar, side chain modification and biosynthetic modification.

The cyclic decapeptides, mixtures thereof or modifications thereof can be formulated into a suitable composition for use on solid matrixes. The composition can be suitably formulated to improve matrix adhesion, solubility, activity, stability and/or limit toxicity. Formulations can contain biological salts, lipids or lipid derivatives, polysaccharides or polysaccharide derivatives, sugars or sugar derivatives, bio-friendly or approved GRAS additives.

A surfactant can be used as a wetting, solubilizing and penetrating agent. Suitable surfactants include peptide derived surfactants (e.g. surfactin and iturin), non-ionic surfactants, anionic surfactants and amphoteric surfactants, such as cholic acids, alkyl sulphate salts, alkylsulfonic acid salts, alkylarylsulfonic acid salts, alkyl aryl ethers and their polyoxyethylene derivatives, polyethylene glycol ethers, polyol esters and sugar alcohol derivatives.

Other components of the formulation can include additional surface active agents, solvents, cosolvents, dyes, U.V. (ultra-violet) protectants, antioxidants, stickers, spreaders, anti-foaming agents, preservatives, humectants, buffers, wetting agents, dispersants, fixing agents, disintegrators, acid solubilisers or other components which facilitate handling and applications. These carriers, diluents, auxiliary agents and so forth are preferably selected to optimize the antimicrobial action on selected solid matrixes.

Other auxiliary agents can include, for example, adhesive agents and dispersing agents, such as casein, polysaccharides (e.g. powdered starch, gum arabic, cellulose derivatives, alginic acid, chitin), lignin derivatives and synthetic water-soluble polymers (e.g. polyvinyl alcohol, polyvinyl pyrolidone, polyacrylic acid), salts (e.g. citrate, chloride, sulphate, acetate, ammonium, bicarbonate, phosphate salts) and stabilizers such as PAP (isopropyl acid phosphate), BHT (2,6-di-tert-butyl-4-methylphenol), BHA (2-3-tert-butyl-4-methyoxyphenol), vegetable oils, mineral oils, phospholipids, waxes, fatty acids and fatty acid esters.

The composition can also include one or more other antimicrobial/antibiotic or antifungal compounds, including natural peptides, lipopeptides or antibiotics from animal, microbial or plant origin or chemically produced fungicides or antibiotics. For example, the composition can include a tyrocidine-gramicidin (termed tyrothricin) complex.

The invention will now be described in more detail by way of the following non-limiting examples.

Examples

Methods and Materials
Preparation of Solid Matrixes Containing Cyclodecapeptides Different polymer matrixes (polymer filters, nanospun membranes/films and 96-well plates) were incubated in a 50 µg/mL tyrocidine (Trc) or gramicidin S (GS) solution in high purity water (HP water generated via a MilliQ™ system) containing 2% ethanol for one hour, after which they were rinsed with HP water for two minutes. Thereafter, the filters (plates or nanofiber sheets) were dried overnight in a 55±5° C. oven and prepared for antibacterial and haemolytic assays. Absorbance measurements were taken of the peptide-containing incubation solution before and after incubation at 230 nm, and the amount of peptide bound to the matrixes was calculated using the equation $(A_{230}+0.0053)/0.015=[Trc]$ µg/mL or $(A_{230}-0.019)/0.0032=[GS]$ µg/mL. Polymer matrixes used included filters from mixed nitrocellulose/cellulose acetate esters (HAWP pore size 0.45 µm; GSWP, pore size 0.22 µm), polyvinylidene difluoride (GVHP, pore size 0.22 µm; HVLP, pore size 0.45 µm), polycarbonate (PC, pore size 0.45 µm), cellulose acetate esters (CA, pore size 0.45 µm) and cellulose filters (CL) (Table 1 shows some examples). HAWP, GSWP, HVLP and GSWP filters were supplied by Waters-Millipore (Milford, USA). PC filters were supplied by Nuclepore Corp (Plesanton, Calif., USA). CA acetate and HDC disks were provided by Sartorius (Gottingen, Germany). CL filters (MN 615/No 1) were obtained from Macherey-Nagel (Duren, Germany). Other matrixes that were tested included high density cellulose (packaging material), nanospun films/membranes of polymethyl methacrylate (PMM) with 1-10% chitin and cellulose with 1-10% chitin provide by M Lutz, Polymer Chemistry, University of Stellenbosch, and Nunc™ 96-well microplates consisting of polypropylene (PP) or low protein-binding polystyrene (PS) provided by AEC Amersham (Johannesburg, South Africa).

TABLE 1

Characteristics and conventional use of selected filters utilised in this study as example materials for treatment with cyclodecapeptides

| Filter name | Monomer structure(s) | Protein binding | Conventional use |
|---|---|---|---|
| Hydrophilic character | | | |
| Mixed cellulose ester-cellulose acetate and nitrocellulose (GSWP, HAWP) | [structure] | High Binding | Buffer/solvent filtration, unsuitable for protein recovery |
| Cellulose acetate (CA) | [structure] | Very low binding | Filtration of tissue culture media and sensitive biological samples |
| High density cellulose (HDC) | [structure] | Unknown | Packaging |
| Cellulose (CL) | | Extremely low non-specific binding | Applications where low non-specific binding is desired |
| Polivinylidene difluoride (HVLP) | [structure] | Low non-specific binding | General biological filtration where high protein recovery is desired |

TABLE 1-continued

Characteristics and conventional use of selected filters utilised in this study as example materials for treatment with cyclodecapeptides

| Filter name | Monomer structure(s) | Protein binding | Conventional use |
|---|---|---|---|
| *Hydrophobic character* | | | |
| Polivinylidene difluoride (GVHP) | [-CH$_2$-CF$_2$-]$_n$ | Low non-specific binding | General biological filtration where high protein recovery is desired |
| Polycarbonate (PC) | bisphenol A carbonate repeat unit | Low non-specific binding | General sterile filtration |

Physical and Chemical Analysis Peptide-Treated Filters

To confirm the presence of peptides on the filters, ninhydrin (0.2% in 95% ethanol) was sprayed on the filters and the colour developed at 50-60° C. To further assess the presence of tyrocidines on the CL filters, peptide was desorbed by incubation in 50% (v/v) acetonitrile for 5 days after which the solution was removed, centrifuged at 1200×g for 10 min, and the supernatant was collected and freeze-dried. The amount of peptides was determined by weighing and the presence of peptide and peptide identity was determined with ultra-performance liquid chromatography linked to electrospray mass spectrometry (UPLC-ESMS) using Acquity UPLC linked to Waters Q-TOF Ultima mass spectrometer with an electrospray ionisation source. The UPLC-ESMS methodology which was used is described by Vosloo et al. (2013), Microbiology 159, 2200-2211, DOI: 10.1099/mic.0.068734-0.

The wettability of untreated and GS- and Trc-treated filters were determined to ascertain the effect the peptides have on the hydrophobicity of the filters. Water containing blue food colouring (50 μL) was pipetted onto untreated and treated filters and the filters were monitored for the drop size and time to complete absorption.

Scanning electron microscopy (SEM) was performed to assess the surface structure of treated and untreated filters for the possible changes brought about by treating the filters with a tyrocidine extract. Filters were dried completely to remove any moisture that could interfere with the SEM signal, by placing them under vacuum and in a desiccator with phosphorus pentoxide. Samples were then mounted on stubs covered in double-sided carbon isolation tape and subsequently coated with a thin layer of gold to make the surface of the sample electrically-conductive. SEM images were obtained with a Leo® 1430VP SEM. Conditions during the surface analysis were 7 kV and 1.5 nA for the beam conditions, a spot size of 145-155 nm and a working distance of 13 mm.

Antibacterial Growth Assay

*Micrococcus luteus* NCTC 8340 was cultured from a freezer stock on Luria Bertani plates (LB: 1% (w/v) NaCl (Merck), 1% (w/v) tryptone (Merck), 0.5% (w/v) yeast extract (Merck), 1.5% (w/v) agar (BioLab) in analytical grade water) and incubated at 37° C. for a period of 48 hours. A colony inoculate in 20 mL of sterile LB broth was incubated at 37° C. until an $A_{620}=0.6$ was reached. Peptide-treated matrix and a control untreated matrix were transferred to a LB agar plate (high nutrient environment). The *M. luteus* culture was diluted to $A_{620}$ of 0.2, further diluted (2000-10000 fold) and transferred to both treated and untreated filters on the LB plate. Plates were incubated for 48 hours at 37° C., after which the matrixes were inspected for the number of colony forming units (CFU).

Cell Viability Assay

Treated and untreated matrixes (filters, membrane and films) were punched into 5 mm disks and triplicate disks were transferred to black 98-well microplates. A mid-log phase *M. luteus* culture was diluted with LB media to $A_{620}$ of 0.20 (1.3×10$^7$ CFU/mL). Each well received 54 of the diluted culture (±6.6×10$^2$ CFUs) on top of the 5 mm disk. The plate was incubated at 37° C. for one hour after which 90 μL phosphate-buffered saline (PBS) and 10 μL CellTiter-Blue® Reagent was added to each well. The plate was again incubated for 2 hours at 37° C. After the one hour incubation in the low nutrient environment, the fluorescence was determined at an excitation wavelength of 530 nm and emission wavelength of 590 nm. The fluorescence reading was taken with a Varioskan™ Multimode reader from Thermo Scientific™ controlled by Skanit Software 2.4.1 from Thermo Electron. Each plate was shaken for 5 seconds before measurements were taken at 25° C.

Cell viability was calculated using the equation:

$$\% \text{ Viability} = 100 \times \frac{\text{Fluorecence in well} - \text{background}}{\text{Average Fluorecence of Controls} - \text{background}}$$

Haemolytic Assay

Fresh blood from anonymous donors (obtained from the Western Cape Blood transfusion Service, South Africa) was transferred to a sterile Falcon® tube, filled with sterile phosphate buffered saline (PBS: 4.0% (w/v) NaCl, 0.1% (w/v) KC, 0.72% (w/v) Na$_2$HPO$_4$, 0.1% (w/v) KH$_2$PO$_4$, pH 7.2, 5× concentrated stock solution) and centrifuged at 1200×g for 3 minutes. The supernatant was removed and the process repeated. The supernatant was removed once again and remaining blood cells were used for the assays. A clear 96-well microplate was used for this assay. Three disks of each of the matrixes (treated and untreated) were placed into the wells and 4 wells received 10 μL of gramicidin S as positive haemolytic control (1.0 mg/mL). Blood (100 μL at 2% hematocrit) was pipetted into each of the wells, after which the plates were sealed and incubated at 37° C. for 2 hours. Following the incubation, the plates were centrifuged for 6 minutes at 300×g. PBS (90 µL) was added to each well of a new plate and 10 µL of the supernatant from each of the wells of the incubated plate was transferred to the PBS. The absorbance was measured at 595 nm. Percentage haemolysis was calculated by adapting an equation used for dose response assays (Rautenbach, Gerstner, Vlok, Kulenkamff and Westerhoff, 2005, Anal. Biochem. 350:81-90):

$$\% \text{ Hemolysis} = 100 \times \frac{\text{Absorbance of well} - \text{background}}{\text{Average Absorbance of 100\% lysis}}$$
$$(GS \text{ containing wells}) - \text{background}$$

A standard curve of tyrocidine doubling dilution (dose response), starting at 20 µg/mL, was used to determine the amount of Tres leading to lysis. Lysis was determined from the linear part of the dose-response curve using the equation: (% haemolysis−2.38)/5.74=[Trc] µg/mL. GS haemolysis proved to be insensitive below 10 µg/mL.

Stability Testing

CL filters (100 mm diameter CL with or without 50 µg/mL tyrocidine treatment) were challenged with multiple wash steps. CL filters were placed in 100 mL of HP water and washed for 1 minute, after which they were transferred to fresh HP water and washed again. This procedure was repeated 12 times.

Solvent-challenges were performed on CL filters when placed in 100 mL 100% acetonitrile (ACN) or HP water containing either 2% NaCl, 1% triethylamine (TEA), 1% trifluoroacetic acid (TFA) or 50% ACN and washed for 1 minute.

The temperature challenges were performed on CL filters for 1 minute with 100 mL HP water heated to 25° C., 40° C., 60° C., 80° C. and 100° C.

The pH stability of the Trc treated CL filters (100 mm) was determined by exposing the filters to a range of pH values. The pH of wash solvent (100 mL HP water) was adjusted with HCl for pH 1, pH 3 and pH 5 and HCl/NaOH to obtain pH 7 and NaOH for pH 9, pH 11 and pH 13.

Both peptide-treated and untreated filters were subjected to the wash treatments. After treatment, the filters were washed (one wash with 100 mL HP water) and dried overnight (16±1 hours) in a low temperature oven (55±5° C.). The change in retained activity was studied with the haemolytic assay and the CFU antimicrobial growth assay or vitality assay as previously described.

Character of Peptide Treated Polymer and Paper Filters

Solid matrixes were chosen to cover a range of polarities, filter characteristics and conventional applications (Table 1). The amount of peptide adsorbed was determined with change in absorbance in the incubation solution and haemolysis assay. The amount of Trc adsorbed was calculated to between 1-4 µg/cm² (Table 2). The haemolysis assay generally gave lower values that the $A_{230}$ assay, probably because it is less sensitive or because petide were bound in a way that did not elicit haemolytic activity. The amount of GS retained, based on the absorbance method, was determined for GVHP (5.3±1.1 µg/cm²), HVLP (2.8±0.6 µg/cm²) and polycarbonate (1.2±2.2 µg/cm²). It was not possible to determine the GS due to the release of an absorbing component from the other filters. The haemolysis assay was insensitive, as GS only started to lyse red blood cells at >10 µg/mL.

TABLE 2

Summary of results obtained in methods utilized to quantify the peptide adsorbed to the different filters treated with Trc extract

| Method of quantification | Positive Control | Mixed CL esters HAWP (0.45 µm) | Mixed CL esters GSWP (0.22 µm) | HVLP (0.45 µm) | GVHP (0.22 µm) | Polycarbonate | Cellulose Acetate | HDC[b] | Cellulose |
|---|---|---|---|---|---|---|---|---|---|
| Absorbance ($A_{230}$) µg/cm² | 50[a] | 3.3 ± 0.7 | 3.4 ± 2.4 | 1.8 ± 1.0 | 1.6 ± 0.8 | 0.9 ± 0.5 | na | na | na |
| Ninhydrin | Purple | nd | nd | nd | nd | nd | nd | nd | Purple |
| Desorption[b] µg/cm² | — | — | — | — | — | — | — | — | 3.8 |
| Hemolysis assay | — | <0.5 | <1 | 1.1 ± 1.1 | 0.9 ± 0.7 | <0.5 | <0.5 | 2.2 ± 1.3 | 3.6 ± 1.6 |

[a]Trc concentration in µm/mL in incubation solution
[b]Desorption was achieved by incubating cellulose filters in 50% (v/v) acetonitrile for 5 days
nd = not detected;
— = not determined;
na = not applicable Desorption of the Trc extract was done to confirm the presence and identity of the adsorbed peptide on the filters. This was conducted in 50% ACN (v/v), since the peptide readily dissolves in the solvent and accordingly aids desorption of the peptide. The UPLC-MS analysis performed on the desorption extract of peptide from the treated cellulose filters confirmed the presence of the major tyrocidines and tryptocidines (FIG. 1A), all of which are present in the original peptide extract used for the treatment of the solid surfaces (FIG. 1B). Peptides with modifications, such as hydroxylation, oxidation, deamination and glycosylation (via Maillard reaction with degraded/hydrolysed cellulose) were not observed.

The wettability, an indicator of hydrophilic/hydrophobic character, could possibly be altered by the adsorption of peptide, and this change in character would be an indication of the orientation in which in the peptide adsorbed to the various filters. The wettability of untreated and treated filters was determined (Table 3) and the untreated filters were rated in terms of hydrophobicity based on the time it took for a water droplet to completely absorb into the filter. The cellulose filters were observed to be very hydrophilic (absorbed water droplet in less than 10 seconds), followed by HAWP, GSWP, CA, HVLP and then GVHP. HDC and PC were observed to be hydrophobic, as the water droplet were not absorbed by 30 minutes. Trc extract- and GS-treated PC, HDC and CL filters showed no visible change in hydrophobic/hydrophilic nature, with HDC showing only a slight increase in hydrophilicity with GS treatment. Trc treatment made CA much more hydrophilic, while GS also lead to an increase in hydrophilicity, indicating the exposure of the polar amino acids to the surface. Trc made the HAWP filters more hydrophobic, whereas the gramicidin S made the filter more hydrophilic. Trc and GS treatment increased the hydrophobicity of the rest of the filters, indicating interaction with polar amino acid residues in these peptides and exposure of the hydrophobic residues to the surface.

interact with and lyse the target cells. Due to the hydrophilic nature of the filter, the tyrocidines are most likely to be adsorbed to the filter via the hydrophilic residues in the peptide, leaving the hydrophobic residues of the peptide exposed to interact with the target cells and cause the observed lysis. Alternatively, it could be that aggregated

TABLE 3

Wettability characteristics of selected filters utilised in this study as example materials for treatment with cyclodecapeptides

| Wettability measurement | Untreated filters | Trc treated filters | Trc induced change in hydrophobicity | GS treated filters | GS induced change in hydrophobicity |
|---|---|---|---|---|---|
| Mixed cellulose acetate/nitrocellulose esters (HAWP, 0.45 µm pores) | | | | | |
| Time until absorbed (min) | 2.25 | 2.35 | increase | 2.20 | slight |
| Drop Diameter (cm) | 0.88 | 0.72 | | 0.96 | decrease |
| Mixed cellulose acetate/nitrocellulose esters (GSWP, 0.22 µm pores) | | | | | |
| Time until absorbed (min) | 3.25 | 3.47 | increase | 3.55 | increase |
| Drop Diameter (cm) | 0.81 | 0.89 | | 0.81 | |
| Cellulose Acetate (CA) | | | | | |
| Time until absorbed (min) | 6.15 | 1.49 | decrease | 5.01 | decrease |
| Drop Diameter (cm) | 0.85 | 1.01 | | 0.85 | |
| High density cellulose (HDC) | | | | | |
| Time until absorbed (min) | >30 | >30 | No change | >30 | slight |
| Drop Diameter (cm) | 0.80 | 0.80 | | 0.94 | increase |
| Cellulose (CL, No 1) | | | | | |
| Time until absorbed | <10 s | <10 s | no change | <10 s | no change |
| Drop Diameter (cm) | >1 | >1 | | >1 | |
| Polyvinylidene difluoride (HVLP, 0.45 µm pores) | | | | | |
| Time until absorbed (min) | 7.26 | 10.34 | increase | 9.20 | increase |
| Drop Diameter (cm) | 0.64 | 0.57 | | 0.72 | |
| Polyvinylidene difluoride (GVLP, 0.22 µm pores) | | | | | |
| Time until absorbed (min) | 11.00 | 16.40 | increase | 17.25 | increase |
| Drop Diameter (cm) | 1.00 | 0.73 | | 1.00 | |
| Polycarbonate (PC, 0.45 µm pores) | | | | | |
| Time until absorbed (min) | >30 | >30 | no change | >30 | no change |
| Drop Diameter (cm) | 0.73 | 0.73 | | 0.73 | |

The extent of the change observed in hydrophobic/hydrophilic character would depend on how much of the peptide is a certain orientation. Based on the amphipathic nature of Tres, it can be assumed that an increase in hydrophobicity translates to the peptide binding to the surface with its hydrophilic sequence (Asn-Gln-Tyr-Val-Orn/Lys SEQ ID NOs: 178/179), leaving the hydrophobic sequence (Leu-Phe-Pro-Phe-Phe SEQ ID NO: 180) to be exposed to the water, and vice versa. For GS, the hydrophilic association was most probably via the cationic Orn residues, while hydrophobic association probably took place via the rest of the residues.

Figure 2A:
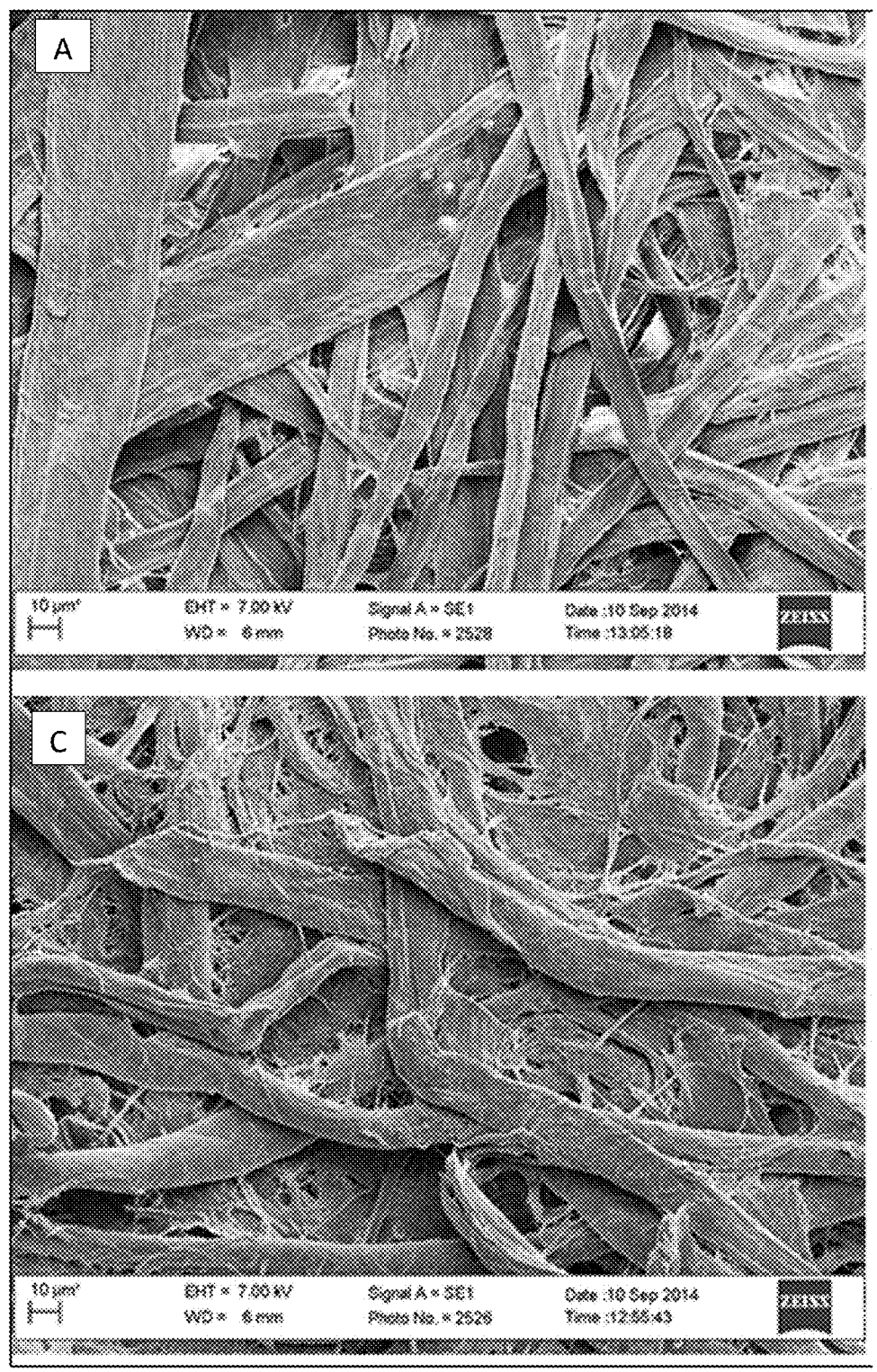
FIG. 2: Scanning electron microscopy images obtained of (A) a cellulose filter, 1 000× magnification, (B) a cellulose Trc treated filter, 1 000× magnification, (C) a Trc treated cellulose filter plus *M. luteus,* 1 000× magnification, and (D) a Trc treated cellulose filter plus erythrocytes, 1 000× magnification.
Figure 2B:
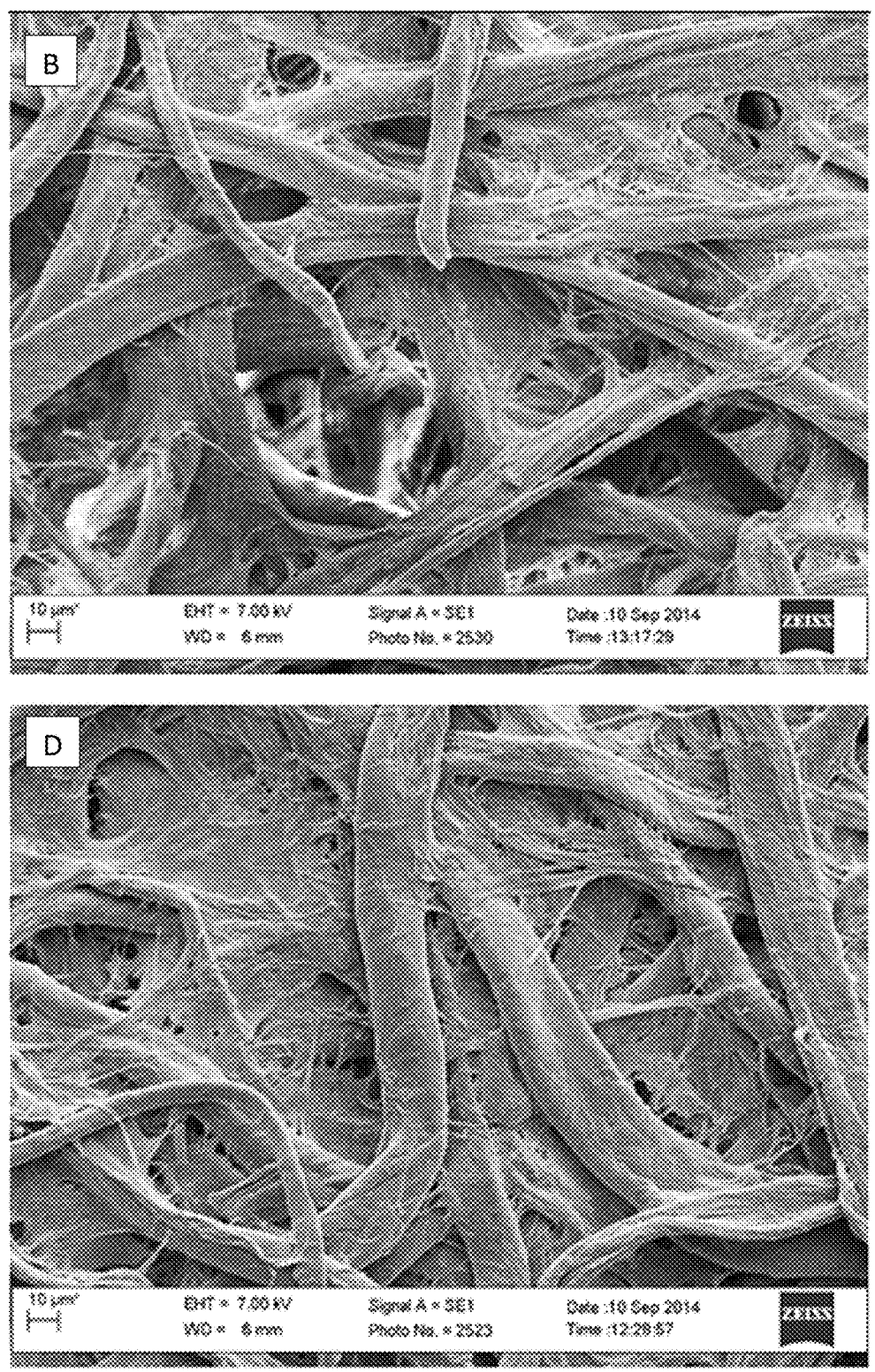

The microscopic SEM analysis of the filters revealed no visual difference between the Trc-treated and untreated filters studied (GSWP, CA and CL), other than a slight bulking of the fibres in Trc-treated filters (results not shown). In all cases, the filter pore structure and structural integrity seemed unchanged. Comparing the Trc-treated CL filter (FIG. 2B) to the CL-treated filters exposed to target cells (FIGS. 2C and 2D), an increase of debris formation on the surface of these filters can be observed but no intact cells, which indicates that cells are lysed. This suggests that the activity of the treated filter is due to the filter possibly being able to entrap the target cells, where the bound Trc can Tres are released from the filter structure, in particular dimeric Trc which is proposed to be the active structure (Munyuki et al. (2013) Biochemistry, 44, 7798-7806), as target cells associate with the Trc-coated surface.

Antimicrobial Activity of Peptide-Treated Polymers and Paper Filters

Antibacterial assays were conducted against the Gram-positive model organism, *M. luteus*, using a range of different matrixes to study the activity of tyrocidines adsorbed to solid surfaces. With the 48 hour growth assays, using a low cell count in a high nutrient environment to support fast growing cells, all the Trc-treated filters, except the CA filters, were protected against overt colonisation by *M. luteus* (Table 4). GS treatment only protected CL, HDC and HVLP against overt colonisation by *M. luteus* (Table 4), indicating that Trc treatment of filters may be more effective than the GS treatment when cells are actively growing.

TABLE 4

Antibacterial activity of Trc- and GS-treated filters against growing *M. luteus* in a high nutrient environment using the CFU growth assay

| Material/matrix (filters) | *M. luteus*, detected CFU/cm$^2$ after 48 h in nutrient rich environment | | | |
|---|---|---|---|---|
| | Control | Trc-treated | Control | GS-treated |
| Mixed nitrocellulose/cellulose acetate esters (HAWP, 0.45 μm) | 28 ± 1 | 1 ± 1 | 4 ± 1 | 4 ± 1 |
| Mixed nitrocellulose/cellulose acetate esters (GSWP 0.22 μm) | 29 ± 2 | 2 ± 2 | 3 ± 2 | 3 ± 1 |
| Cellulose acetate (CA) | 8 ± 2 | 8 ± 2 | 3 ± 1 | 3 ± 1 |
| High density cellulose (HDC) | 43 ± 4 | 0 | 4 ± 1 | 0 |
| Cellulose (CL) | 45 ± 2 | 0 | 3 ± 1 | 0 |
| Polyvinylidene difluoride (HVLP, 0.45 μm) | 27 ± 4 | 0 | 3 ± 1 | 0 |
| Polyvinylidene difluoride (GVHP, 0.22 μm) | 34 ± 1 | 0 | 3 ± 1 | 3 ± 1 |
| Polycarbonate (PC, 0.45 um) | 32 ± 3 | 0 | 3 ± 1 | 4 ± 1 |

Figure 3:
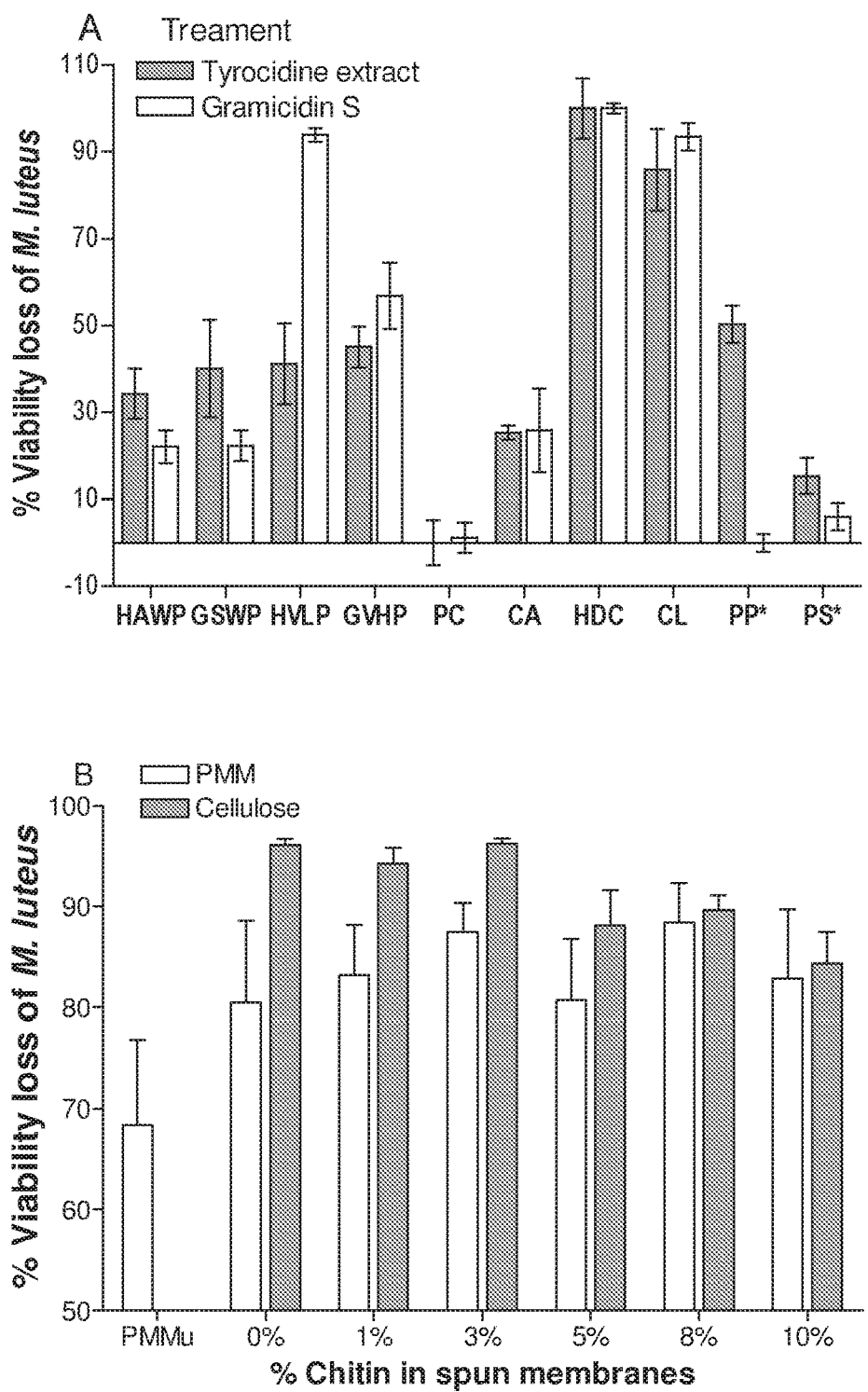
FIG. 3: Comparison of retained antimicrobial activity of different filters (A) and nanofibers (B) treated with the Trc extract or gramicidin S (GS). The bars in (A) marked with * indicate that the treated surface was that of wells in a 96-well plate (not filter) with PS as polystyrene and PP polypropylene. The inhibitory activity was determined in a low nutrient environment with high bacterial cell count ($6.6 \times 10^4$ *M. luteus* cells per well or 5 mm filter disk) using the viability assay. Bars represent the average of 6-9 determinations with standard error of the mean (SEM).

Different filters, surfaces and nanofibers, treated with Trc extract or GS, were assessed for the more direct short-term killing of *M. luteus* (sterilisation) using a low nutrient environment, high cell count and the Alamar Blue vitality assay to assess bacterial metabolism. Good protection of HDC and CL filters was again observed for both the Trc extract and GS treatment (FIG. 3A). GS again showed good protection in the HVLP filter and improved activity in all the other filters except PC. Trc treatment gave similar protection to that of GS, except for HVLP where GS was superior. However, Trc did not prove to be as effective in direct sterilisation, particularly for the more hydrophobic filters (e.g. PC) and filters where it led to increased hydrophobicity of the filters (HAWP, GSWP, HVLP and GSWP) (Tables 4 and 3). This could be due to the limited spreading of the 5 μL culture on the filter, limiting the contact of the bacteria with the rest of the Trc-coated filter, and thus this assay could have underestimated the overall filter activity. The opposite was true for CA, where Trc increased the hydrophilicity dramatically and led to an increased sterilisation as detected with the vitality assay (Tables 3 and 4). Similar sterilisation to CL filters was observed for nanofibre films containing CL when treated with Trc extract (FIG. 3B). The Trc-treated nanofibres containing poly(methyl methacrylate) (PMM) also had a good sterilisation activity, although this was slightly less than the nanofibres with CL. The inclusion of chitin in the nanofibres with CL or PMM did not have a major influence, although high chitin content did lead to some loss of activity (FIG. 3B).

Figure 4:
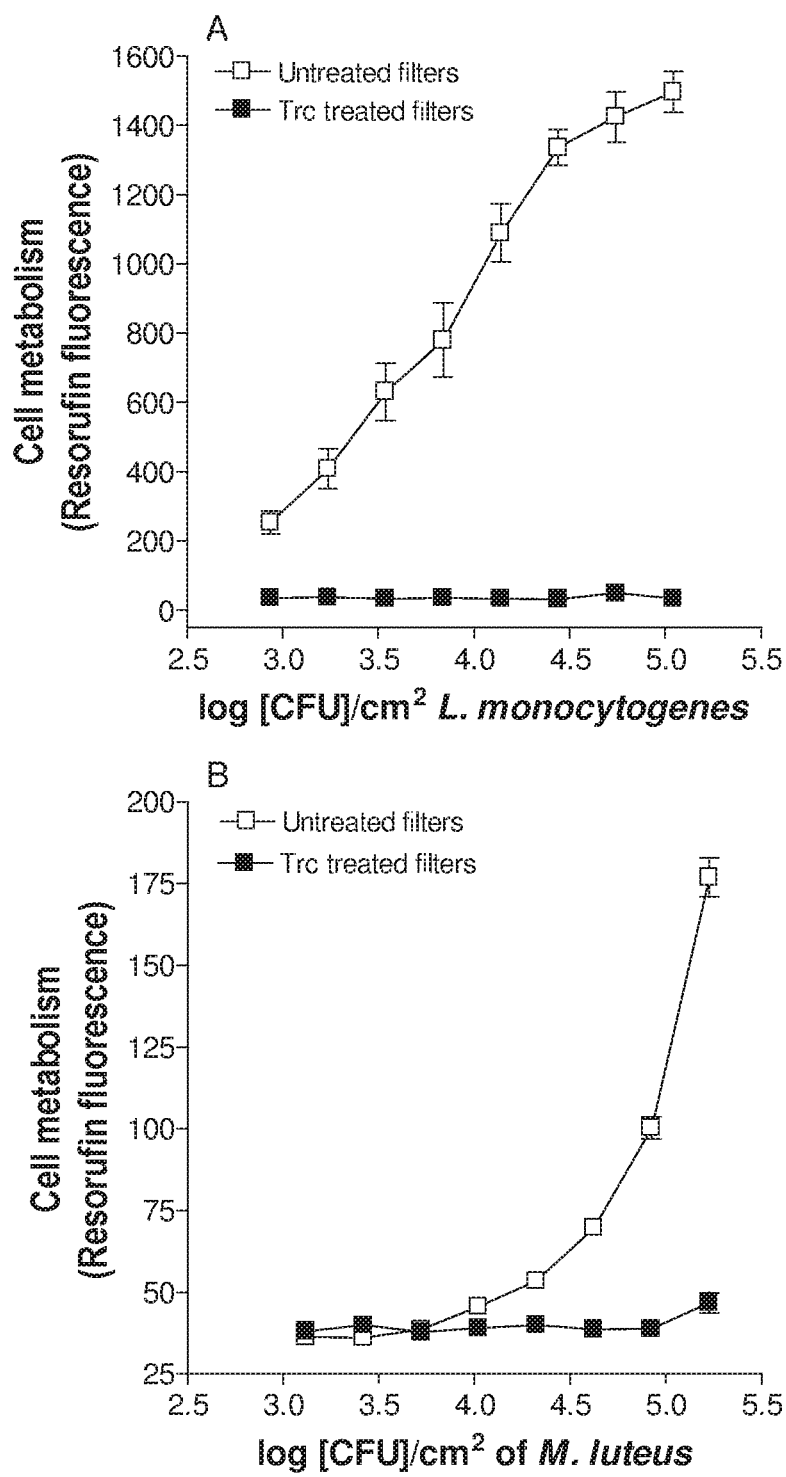
FIG. 4: Challenge of cellulose (CL) filters treated with Trc extract with different concentrations of bacteria showing the sterilisation effectivity as determined with a vitality assay on (A) *Listeria monocytogenes* and (B) *Micrococcus luteus*. Each data point represents the mean of 9 determinations with SEM.

Trc treatment of CL was found to provide sterilisation for a challenge of up to 10$^5$ Gram-positive bacterial cells per cm$^2$, including the food-pathogen *Listeria monocytogenes* (FIG. 4). Overt activity for either GS- or Trc-treated CL filters against Gram-negative organisms, however, was not demonstrated. The filters retained moderate antifungal activity against most environmental fungi, as indicated by a separate study on seed germination using the Trc-treated CL filters as matrix in a highly humid environment (results not shown).

The antibacterial activity observed for the peptide adsorbed to CL and HDC filters, as well as the CL containing nanofibers, bodes well for the application of the these matrixes, since it has been noted that organisms favour attachment to CL surfaces to initiate biofilm formation. It also opens the possibility of using tyrocidines in CL-based protective packaging for spoilable produce. The retained activity against the other synthetic polymer matrices is a good indication of the potential of these cyclic decapeptides to act as solid state sterilisation agents, with a multitude of applications in medicine and industry.

Stability of Peptide Treated Matrices

The CL filters were selected for further stability tests based on the results which showed that Trc best adsorbed to it and maintained activity on these filters over time, with more than 80% of the original activity maintained after 18 months.

Stability of the Trc activity on the CL filters was tested with multiple washes, pH changes, different solvents and temperature changes of the incubation solution. It was found that there was no statistical difference between the 12 washes based on the haemolytic activity of the filters. Regarding the antibacterial activity against *M. luteus*, only one sample, of the three filter disks used for each wash step, with bacterial colonies (10 CFUs on 100 mm filter disk) was observed for filters in washes 1, 4 and 6-12.

Figure 5:
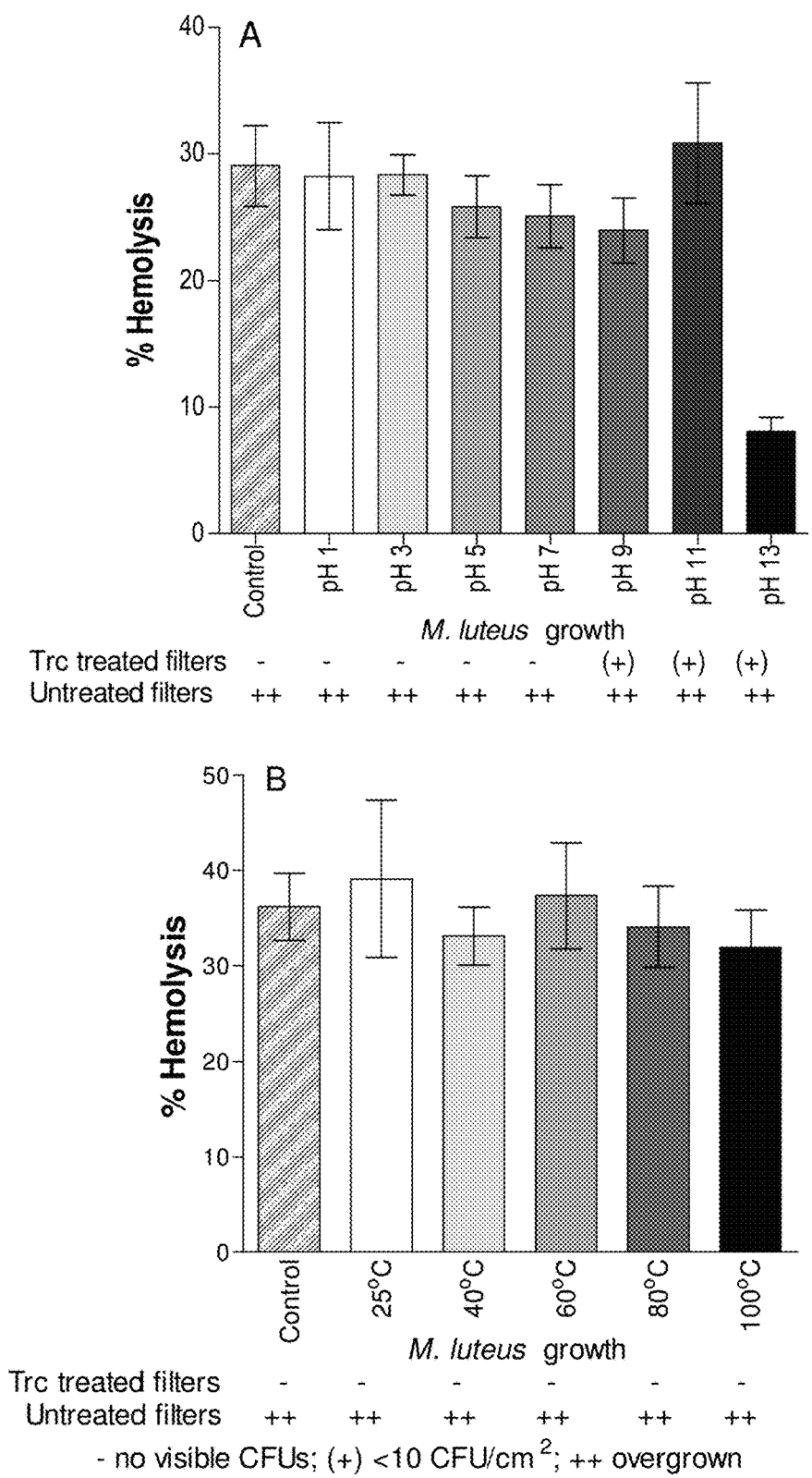
FIG. 5: The effect of (A) pH changes and (B) temperature changes on the amount of tyrocidine retained on 50 µg/mL cellulose filters as determined with a haemolytic assay. Gramicidin S (GS) was used for the positive control of 100% haemolysis observed and 50 µg/mL unwashed cellulose filter as reference point to total amount tyrocidines originally adsorbed. Each data point represents the mean of 3 determinations with SEM.
Figure 6:
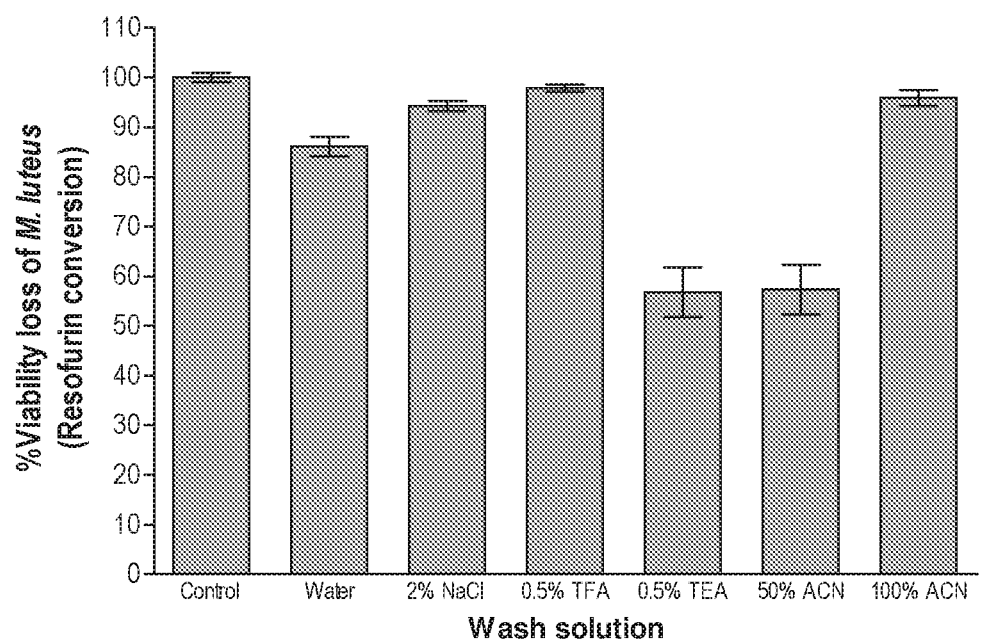
FIG. 6: The effect of washing of cellulose (CL) filters treated with Trc extract with different solvents on the sterility of the filters as determined with a vitality assay with *M. luteus* as bacterial contaminant. Each data point represents the mean of at least 24 determinations with SEM.

The retained activity of the CL filters treated with Trc proved to be remarkably robust, with near full retention of both the indicator haemolytic activity and antibacterial activity over pH 1-11 (FIG. 5A). The change in pH showed only a statistically significant decrease in haemolytic activity of the pH 13-treated filter compared to the other pH-treated filters (FIG. 5A). The antibacterial activity against *M. luteus* showed only one sample of the three filter disks challenged at each of pH 9, 11, 13 with bacterial colonies (10 CFUs on 100 mm filter disk). Slight deterioration of filter integrity was observed at pH 11 and pH 13. There was no statistically significant difference observed for the haemolytic activity or antibacterial activity by the high temperature wash challenge and of Trc-treated filters (FIG. 5B). The sterilising activity of the CL filter also remained stable with salt, dilute acid and organic solvent washes (FIG. 6). The only solvents that did influence the activity were 50% acetonitrile and the highly basic 1% TEA, which led to an about 40% loss of activity.

The stability tests indicate that tyrocidines remain adsorbed to the cellulose filter and maintain activity regardless of changes in pH and temperature, as well as after multiple wash steps with water, salt, dilute acid and organic solvent.

The composition of the invention provides a natural alternative with robust solid state antimicrobial character to industrial disinfection agents, without the detrimental side effects associated therewith.

The invention claimed is:

1. A method for preventing microbial growth on a manufactured product, the method comprising the step of:
   (i) applying a composition comprising as active agent cyclic decapeptides comprising an amino acid sequence of cyclo($X_{10}$-$X_1$-Leu-D-Phe-Pro-$X_2$-$x_3$-Asn-Gln-$X_6$), where
   $X_{10}$ is Val, Leu or Ile;
   $X_1$ is Orn or Lys;
   $X_2$ is Val, Leu, Ile, Phe, Trp or Tyr;
   $x_3$ is the D-isomer of Val, Leu, Ile, Phe, Trp or Tyr; and
   $X_6$ is Tyr, Phe or Trp,
   to a surface of the manufactured product;
   wherein the cyclic decapeptides absorb into or adsorb onto the surface to dry; and
   wherein the cyclic decapeptides remain adhered to the surface of the manufactured product when in contact with water, a salt solution, or a dilute acid; and
   wherein the manufactured product is not casein.

2. The method according to claim 1, wherein:
   $X_{10}$ is Val, Leu or Ile;
   $X_1$ is Orn or Lys;
   $X_2$ is Trp or Phe;
   $x_3$ is D-Trp or D-Phe; and
   $X_6$ is Tyr, Trp or Phe.

3. The method according to claim 1, wherein the cyclic decapeptides have an amino acid sequence selected from any one of SEQ ID NOS: 6-167.

4. The method according to claim 1, wherein the composition contains a mixture of any two or more different cyclic decapeptides having an amino acid sequence selected from any one of SEQ ID NOS: 6-167.

5. The method according to claim 1, wherein the manufactured product is made from a polymer.

6. The method according to claim 5, wherein the polymer is a natural polymer.

7. The method according to claim 5, wherein the polymer is a synthetic or semi-synthetic polymer.

8. The method according to claim 5, wherein the manufactured product is made from a combination of natural, synthetic and/or semi-synthetic polymers.

9. The method according to claim 1, wherein the manufactured product is selected from the group consisting of a wound dressing or part thereof, packaging, a container, wrapping, a work surface, a filter, a catheter and a pipe.

10. The method according to claim 1, wherein the microbial growth to be prevented is fungal and/or bacterial growth.

11. The method according to claim 1, wherein the composition is applied to the surface of the manufactured product in a liquid form, gel or mist or during preparation of the manufactured product.

12. A manufactured product which has been treated according to the method of claim 1 so that cyclic decapeptides with an amino acid sequence of cyclo($X_{10}$-$X_1$-Leu-D-Phe-Pro-$X_2$-$x_3$-Asn-Gln-$X_6$), wherein
   $X_{10}$ is Val, Leu or Ile;
   $X_1$ is Orn or Lys;
   $X_2$ is Val, Leu, Ile, Phe, Trp or Tyr;
   $x_3$ is the D-isomer of Val, Leu, Ile, Phe, Trp, or Tyr; and
   $X_6$ is Tyr, Phe, or Trp,
   are absorbed into or adsorbed onto a surface of the manufactured product and have dried thereon, and remain adhered to the surface of the manufactured product when in contact with water, a salt solution, or a dilute acid.

13. A method for providing a surface of a manufactured product with antimicrobial activity, the method comprising the step of:
   (i) treating a matrix of the manufactured product with a composition which comprises cyclic decapeptides which have an amino acid sequence of cyclo($X_{10}$-$X_1$-Leu-D-Phe-Pro-$X_2$-$x_3$-Asn-Gln-$X_6$), where
   $X_{10}$ is Val, Leu or Ile;
   $X_1$ is Orn or Lys;
   $X_2$ is Val, Leu, Ile, Phe, Trp or Tyr;
   $x_3$ is the D-isomer of Val, Leu, Ile, Phe, Trp, or Tyr; and
   $X_6$ is Tyr, Phe, or Trp;
   wherein the cyclic decapeptides absorb into or adsorb onto the matrix or surface of a manufactured product and dry;
   wherein the cyclic decapeptides remain adhered to the surface of the manufactured product in water, a salt solution, or a dilute acid; and
   wherein the manufactured product is not casein.

14. The method according to claim 1, wherein the composition is applied to the surface of the manufactured product during preparation of the manufactured product.

* * * * *

SEQUENCE LISTING

<160> NUMBER OF SEQ ID NOS: 180

<210> SEQ ID NO 1
<211> LENGTH: 10
<212> TYPE: PRT
<213> ORGANISM: Artificial Sequence

```
<220> FEATURE:
<223> OTHER INFORMATION: Artificial construct; Cyclic polypeptide
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (6)..(6)
<223> OTHER INFORMATION: X2 = V, L, I, F, W or Y
<220> FEATURE:
<221> NAME/KEY: VARIANT
<222> LOCATION: (7)..(7)
<223> OTHER INFORMATION: X3 = v, L, I, F, W, Y, O or K
<220> FEATURE:
<221> NAME/KEY: VARIANT
<222> LOCATION: (8)..(8)
<223> OTHER INFORMATION: X4 = N, Q or L
<220> FEATURE:
<221> NAME/KEY: VARIANT
<222> LOCATION: (9)..(9)
<223> OTHER INFORMATION: X5 = Q, v, L or I
<220> FEATURE:
<221> NAME/KEY: VARIANT
<222> LOCATION: (10)..(10)
<223> OTHER INFORMATION: X6 = Y, F, W or P

<400> SEQUENCE: 1

Val Xaa Leu Phe Pro Xaa Xaa Xaa Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (6)..(6)
<223> OTHER INFORMATION: X7 = W or F
<220> FEATURE:
<221> NAME/KEY: VARIANT
<222> LOCATION: (7)..(7)
<223> OTHER INFORMATION: X8 = w or f
<220> FEATURE:
<221> NAME/KEY: VARIANT
<222> LOCATION: (10)..(10)
<223> OTHER INFORMATION: X9 = Y, W, or F

<400> SEQUENCE: 2

Val Xaa Leu Phe Pro Xaa Xaa Asn Gln Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: VARIANT
<222> LOCATION: (2)..(2)
<223> OTHER INFORMATION: X1 = O or K
<220> FEATURE:
<221> NAME/KEY: VARIANT
<222> LOCATION: (7)..(7)
<223> OTHER INFORMATION: X1 = O or K

<400> SEQUENCE: 3
```

```
Val Xaa Leu Phe Pro Val Xaa Leu Phe Pro
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 4

Val Xaa Leu Phe Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Artificial construct; Cyclic polypeptide

<400> SEQUENCE: 5

Phe Phe Asn Gln Tyr
1               5

<210> SEQ ID NO 6
<211> LENGTH: 10
<212> TYPE: PRT
<213> ORGANISM: Bacillus aneurinolyticus

<400> SEQUENCE: 6

Val Lys Leu Phe Pro Trp Trp Asn Gln Tyr
1               5                   10

<210> SEQ ID NO 7
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 7

Val Xaa Leu Phe Pro Trp Trp Asn Gln Tyr
1               5                   10

<210> SEQ ID NO 8
<211> LENGTH: 10
<212> TYPE: PRT
<213> ORGANISM: Bacillus aneurinolyticus

<400> SEQUENCE: 8

Val Lys Leu Phe Pro Trp Phe Asn Gln Tyr
1               5                   10

<210> SEQ ID NO 9
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn
```

-continued

```
<400> SEQUENCE: 9

Val Xaa Leu Phe Pro Trp Phe Asn Gln Tyr
1               5                   10

<210> SEQ ID NO 10
<211> LENGTH: 10
<212> TYPE: PRT
<213> ORGANISM: Bacillus aneurinolyticus

<400> SEQUENCE: 10

Val Lys Leu Phe Pro Phe Trp Asn Gln Tyr
1               5                   10

<210> SEQ ID NO 11
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 11

Val Xaa Leu Phe Pro Phe Trp Asn Gln Tyr
1               5                   10

<210> SEQ ID NO 12
<211> LENGTH: 10
<212> TYPE: PRT
<213> ORGANISM: Bacillus aneurinolyticus

<400> SEQUENCE: 12

Val Lys Leu Phe Pro Phe Phe Asn Gln Tyr
1               5                   10

<210> SEQ ID NO 13
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 13

Val Xaa Leu Phe Pro Phe Phe Asn Gln Tyr
1               5                   10

<210> SEQ ID NO 14
<211> LENGTH: 10
<212> TYPE: PRT
<213> ORGANISM: Bacillus aneurinolyticus

<400> SEQUENCE: 14

Val Lys Leu Phe Pro Tyr Trp Asn Gln Tyr
1               5                   10

<210> SEQ ID NO 15
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn
```

```
<400> SEQUENCE: 15

Val Xaa Leu Phe Pro Tyr Trp Asn Gln Tyr
1               5                   10

<210> SEQ ID NO 16
<211> LENGTH: 10
<212> TYPE: PRT
<213> ORGANISM: Bacillus aneurinolyticus

<400> SEQUENCE: 16

Val Lys Leu Phe Pro Tyr Phe Asn Gln Tyr
1               5                   10

<210> SEQ ID NO 17
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 17

Val Xaa Leu Phe Pro Tyr Phe Asn Gln Tyr
1               5                   10

<210> SEQ ID NO 18
<211> LENGTH: 10
<212> TYPE: PRT
<213> ORGANISM: Bacillus aneurinolyticus

<400> SEQUENCE: 18

Val Lys Leu Phe Pro Phe Tyr Asn Gln Tyr
1               5                   10

<210> SEQ ID NO 19
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 19

Val Xaa Leu Phe Pro Phe Tyr Asn Gln Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 20

Val Lys Leu Phe Pro Trp Tyr Asn Gln Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
```

<222> LOCATION: (2)..(2)
<223> OTHER INFORMATION: Orn

<400> SEQUENCE: 21

Val Xaa Leu Phe Pro Trp Tyr Asn Gln Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 22

Leu Lys Leu Phe Pro Trp Trp Asn Gln Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 23

Leu Xaa Leu Phe Pro Trp Trp Asn Gln Tyr
1               5                   10

<210> SEQ ID NO 24
<211> LENGTH: 10
<212> TYPE: PRT
<213> ORGANISM: Bacillus aneurinolyticus

<400> SEQUENCE: 24

Leu Lys Leu Phe Pro Trp Phe Asn Gln Tyr
1               5                   10

<210> SEQ ID NO 25
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 25

Leu Xaa Leu Phe Pro Trp Phe Asn Gln Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 26

Leu Lys Leu Phe Pro Phe Trp Asn Gln Tyr
1               5                   10

<210> SEQ ID NO 27

```
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 27

Leu Xaa Leu Phe Pro Phe Trp Asn Gln Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 28

Leu Lys Leu Phe Pro Phe Phe Asn Gln Tyr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 29

Leu Xaa Leu Phe Pro Phe Phe Asn Gln Tyr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 30

Leu Lys Leu Phe Pro Tyr Trp Asn Gln Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 31

Leu Xaa Leu Phe Pro Tyr Trp Asn Gln Tyr
1               5                   10

<210> SEQ ID NO 32
<211> LENGTH: 10
<212> TYPE: PRT
```

```
<213> ORGANISM: Artificial Sequence
<220> FEATURE:
<223> OTHER INFORMATION: Artificial construct; Cyclic polypeptide

<400> SEQUENCE: 32

Leu Lys Leu Phe Pro Tyr Phe Asn Gln Tyr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 33

Leu Xaa Leu Phe Pro Tyr Phe Asn Gln Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 34

Leu Lys Leu Phe Pro Phe Tyr Asn Gln Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 35

Leu Xaa Leu Phe Pro Phe Tyr Asn Gln Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 36

Leu Lys Leu Phe Pro Trp Tyr Asn Gln Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
```

<223> OTHER INFORMATION: Orn

<400> SEQUENCE: 37

Leu Xaa Leu Phe Pro Trp Tyr Asn Gln Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 38

Ile Lys Leu Phe Pro Trp Trp Asn Gln Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 39

Ile Xaa Leu Phe Pro Trp Trp Asn Gln Tyr
1               5                   10

<210> SEQ ID NO 40
<211> LENGTH: 10
<212> TYPE: PRT
<213> ORGANISM: Bacillus aneurinolyticus

<400> SEQUENCE: 40

Ile Lys Leu Phe Pro Trp Phe Asn Gln Tyr
1               5                   10

<210> SEQ ID NO 41
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 41

Ile Xaa Leu Phe Pro Trp Phe Asn Gln Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 42

Ile Lys Leu Phe Pro Phe Trp Asn Gln Tyr
1               5                   10

<210> SEQ ID NO 43
<211> LENGTH: 10

```
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 43

Ile Xaa Leu Phe Pro Phe Trp Asn Gln Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 44

Ile Lys Leu Phe Pro Phe Phe Asn Gln Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 45

Ile Xaa Leu Phe Pro Phe Phe Asn Gln Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 46

Ile Lys Leu Phe Pro Tyr Trp Asn Gln Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 47

Ile Xaa Leu Phe Pro Tyr Trp Asn Gln Tyr
1               5                   10

<210> SEQ ID NO 48
<211> LENGTH: 10
<212> TYPE: PRT
<213> ORGANISM: Artificial Sequence
```

```
<220> FEATURE:
<223> OTHER INFORMATION: Artificial construct; Cyclic polypeptide

<400> SEQUENCE: 48

Ile Lys Leu Phe Pro Tyr Phe Asn Gln Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 49

Ile Xaa Leu Phe Pro Tyr Phe Asn Gln Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 50

Ile Lys Leu Phe Pro Phe Tyr Asn Gln Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 51

Ile Xaa Leu Phe Pro Phe Tyr Asn Gln Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 52

Ile Lys Leu Phe Pro Trp Tyr Asn Gln Tyr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
```

```
<400> SEQUENCE: 53

Ile Xaa Leu Phe Pro Trp Tyr Asn Gln Tyr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 54

Val Lys Leu Phe Pro Leu Trp Asn Gln Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 55

Val Xaa Leu Phe Pro Leu Trp Asn Gln Tyr
1               5                   10

<210> SEQ ID NO 56
<211> LENGTH: 10
<212> TYPE: PRT
<213> ORGANISM: Bacillus aneurinolyticus

<400> SEQUENCE: 56

Val Lys Leu Phe Pro Leu Phe Asn Gln Tyr
1               5                   10

<210> SEQ ID NO 57
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 57

Val Xaa Leu Phe Pro Leu Phe Asn Gln Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 58

Val Lys Leu Phe Pro Leu Tyr Asn Gln Tyr
1               5                   10

<210> SEQ ID NO 59
<211> LENGTH: 10
<212> TYPE: PRT
```

```
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 59

Val Xaa Leu Phe Pro Leu Tyr Asn Gln Tyr
1               5                   10

<210> SEQ ID NO 60
<211> LENGTH: 10
<212> TYPE: PRT
<213> ORGANISM: Bacillus aneurinolyticus

<400> SEQUENCE: 60

Val Lys Leu Phe Pro Trp Trp Asn Gln Trp
1               5                   10

<210> SEQ ID NO 61
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 61

Val Xaa Leu Phe Pro Trp Trp Asn Gln Trp
1               5                   10

<210> SEQ ID NO 62
<211> LENGTH: 10
<212> TYPE: PRT
<213> ORGANISM: Bacillus aneurinolyticus

<400> SEQUENCE: 62

Val Lys Leu Phe Pro Trp Phe Asn Gln Trp
1               5                   10

<210> SEQ ID NO 63
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 63

Val Xaa Leu Phe Pro Trp Phe Asn Gln Trp
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 64

Val Lys Leu Phe Pro Phe Trp Asn Gln Trp
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 65

Val Xaa Leu Phe Pro Phe Trp Asn Gln Trp
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 66

Val Lys Leu Phe Pro Phe Phe Asn Gln Trp
1               5                   10

<210> SEQ ID NO 67
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 67

Val Xaa Leu Phe Pro Phe Phe Asn Gln Trp
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 68

Val Lys Leu Phe Pro Tyr Trp Asn Gln Trp
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 69

Val Xaa Leu Phe Pro Tyr Trp Asn Gln Trp
1               5                   10

<210> SEQ ID NO 70
<211> LENGTH: 10
<212> TYPE: PRT
<213> ORGANISM: Artificial Sequence
```

```
<220> FEATURE:
<223> OTHER INFORMATION: Artificial construct; Cyclic polypeptide

<400> SEQUENCE: 70

Val Lys Leu Phe Pro Tyr Phe Asn Gln Trp
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 71

Val Xaa Leu Phe Pro Tyr Phe Asn Gln Trp
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 72

Val Lys Leu Phe Pro Phe Tyr Asn Gln Trp
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 73

Val Xaa Leu Phe Pro Phe Tyr Asn Gln Trp
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 74

Val Lys Leu Phe Pro Trp Tyr Asn Gln Trp
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
```

```
<400> SEQUENCE: 75

Val Xaa Leu Phe Pro Trp Tyr Asn Gln Trp
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 76

Leu Lys Leu Phe Pro Trp Trp Asn Gln Trp
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 77

Leu Xaa Leu Phe Pro Trp Trp Asn Gln Trp
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 78

Leu Lys Leu Phe Pro Trp Phe Asn Gln Trp
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 79

Leu Xaa Leu Phe Pro Trp Phe Asn Gln Trp
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 80

Leu Lys Leu Phe Pro Phe Trp Asn Gln Trp
1               5                   10
```

```
<210> SEQ ID NO 81
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 81

Leu Xaa Leu Phe Pro Phe Trp Asn Gln Trp
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 82

Leu Lys Leu Phe Pro Phe Phe Asn Gln Trp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 83

Leu Xaa Leu Phe Pro Phe Phe Asn Gln Trp
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 84

Leu Lys Leu Phe Pro Tyr Trp Asn Gln Trp
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 85

Leu Xaa Leu Phe Pro Tyr Trp Asn Gln Trp
1               5                   10

<210> SEQ ID NO 86
```

```
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 86

Leu Lys Leu Phe Pro Tyr Phe Asn Gln Trp
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 87

Leu Xaa Leu Phe Pro Tyr Phe Asn Gln Trp
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 88

Leu Lys Leu Phe Pro Phe Tyr Asn Gln Trp
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 89

Leu Xaa Leu Phe Pro Phe Tyr Asn Gln Trp
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 90

Leu Lys Leu Phe Pro Trp Tyr Asn Gln Trp
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
```

```
<221> NAME/KEY: MOD_RES
<222> LOCATION: (2)..(2)
<223> OTHER INFORMATION: Orn

<400> SEQUENCE: 91

Leu Xaa Leu Phe Pro Trp Tyr Asn Gln Trp
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 92

Ile Lys Leu Phe Pro Trp Trp Asn Gln Trp
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 93

Ile Xaa Leu Phe Pro Trp Trp Asn Gln Trp
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 94

Ile Lys Leu Phe Pro Trp Phe Asn Gln Trp
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 95

Ile Xaa Leu Phe Pro Trp Phe Asn Gln Trp
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 96
```

Ile Lys Leu Phe Pro Phe Trp Asn Gln Trp
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 97

Ile Xaa Leu Phe Pro Phe Trp Asn Gln Trp
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 98

Ile Lys Leu Phe Pro Phe Phe Asn Gln Trp
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 99

Ile Xaa Leu Phe Pro Phe Phe Asn Gln Trp
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 100

Ile Lys Leu Phe Pro Tyr Trp Asn Gln Trp
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 101

Ile Xaa Leu Phe Pro Tyr Trp Asn Gln Trp
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 102

Ile Lys Leu Phe Pro Tyr Phe Asn Gln Trp
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 103

Ile Xaa Leu Phe Pro Tyr Phe Asn Gln Trp
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 104

Ile Lys Leu Phe Pro Phe Tyr Asn Gln Trp
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 105

Ile Xaa Leu Phe Pro Phe Tyr Asn Gln Trp
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 106

Ile Lys Leu Phe Pro Trp Tyr Asn Gln Trp
1               5                   10

<210> SEQ ID NO 107
<211> LENGTH: 10
<212> TYPE: PRT
<213> ORGANISM: Artificial Sequence

```
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 107

Ile Xaa Leu Phe Pro Trp Tyr Asn Gln Trp
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 108

Val Lys Leu Phe Pro Leu Trp Asn Gln Trp
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 109

Val Xaa Leu Phe Pro Leu Trp Asn Gln Trp
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 110

Val Lys Leu Phe Pro Leu Phe Asn Gln Trp
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 111

Val Xaa Leu Phe Pro Leu Phe Asn Gln Trp
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Artificial construct; Cyclic polypeptide
```

<400> SEQUENCE: 112

Val Lys Leu Phe Pro Leu Tyr Asn Gln Trp
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 113

Val Xaa Leu Phe Pro Leu Tyr Asn Gln Trp
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 114

Val Lys Leu Phe Pro Trp Trp Asn Gln Phe
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 115

Val Xaa Leu Phe Pro Trp Trp Asn Gln Phe
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 116

Val Lys Leu Phe Pro Trp Phe Asn Gln Phe
1               5                   10

<210> SEQ ID NO 117
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 117

Val Xaa Leu Phe Pro Trp Phe Asn Gln Phe

```
<210> SEQ ID NO 118
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 118

Val Lys Leu Phe Pro Phe Trp Asn Gln Phe
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 119

Val Xaa Leu Phe Pro Phe Trp Asn Gln Phe
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 120

Val Lys Leu Phe Pro Phe Phe Asn Gln Phe
1               5                   10

<210> SEQ ID NO 121
<211> LENGTH: 10
<212> TYPE: PRT
<213> ORGANISM: Bacillus aneurinolyticus
<220> FEATURE:
<221> NAME/KEY: MOD_RES
<222> LOCATION: (2)..(2)
<223> OTHER INFORMATION: Orn

<400> SEQUENCE: 121

Val Xaa Leu Phe Pro Phe Phe Asn Gln Phe
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 122

Val Lys Leu Phe Pro Tyr Trp Asn Gln Phe
1               5                   10

<210> SEQ ID NO 123
<211> LENGTH: 10
<212> TYPE: PRT
<213> ORGANISM: Artificial Sequence
<220> FEATURE:
```

```
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 123

Val Xaa Leu Phe Pro Tyr Trp Asn Gln Phe
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 124

Val Lys Leu Phe Pro Tyr Phe Asn Gln Phe
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 125

Val Xaa Leu Phe Pro Tyr Phe Asn Gln Phe
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 126

Val Lys Leu Phe Pro Phe Tyr Asn Gln Phe
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 127

Val Xaa Leu Phe Pro Phe Tyr Asn Gln Phe
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Artificial construct; Cyclic polypeptide
```

```
<400> SEQUENCE: 128

Val Lys Leu Phe Pro Trp Tyr Asn Gln Phe
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 129

Val Xaa Leu Phe Pro Trp Tyr Asn Gln Phe
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 130

Leu Lys Leu Phe Pro Trp Trp Asn Gln Phe
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 131

Leu Xaa Leu Phe Pro Trp Trp Asn Gln Phe
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 132

Leu Lys Leu Phe Pro Trp Phe Asn Gln Phe
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 133
```

```
Leu Xaa Leu Phe Pro Trp Phe Asn Gln Phe
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 134

Leu Lys Leu Phe Pro Phe Trp Asn Gln Phe
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 135

Leu Xaa Leu Phe Pro Phe Trp Asn Gln Phe
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 136

Leu Lys Leu Phe Pro Tyr Trp Asn Gln Phe
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 137

Leu Xaa Leu Phe Pro Tyr Trp Asn Gln Phe
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 138

Leu Lys Leu Phe Pro Tyr Phe Asn Gln Phe
1               5                   10

<210> SEQ ID NO 139
<211> LENGTH: 10
```

```
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 139

Leu Xaa Leu Phe Pro Tyr Phe Asn Gln Phe
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 140

Leu Lys Leu Phe Pro Phe Tyr Asn Gln Phe
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 141

Leu Xaa Leu Phe Pro Phe Tyr Asn Gln Phe
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 142

Leu Lys Leu Phe Pro Trp Tyr Asn Gln Phe
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 143

Leu Xaa Leu Phe Pro Trp Tyr Asn Gln Phe
1               5                   10

<210> SEQ ID NO 144
<211> LENGTH: 10
<212> TYPE: PRT
<213> ORGANISM: Artificial Sequence
```

```
<220> FEATURE:
<223> OTHER INFORMATION: Artificial construct; Cyclic polypeptide

<400> SEQUENCE: 144

Leu Lys Leu Phe Pro Phe Phe Asn Gln Phe
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 145

Leu Xaa Leu Phe Pro Phe Phe Asn Gln Phe
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 146

Ile Lys Leu Phe Pro Trp Trp Asn Gln Phe
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 147

Ile Xaa Leu Phe Pro Trp Trp Asn Gln Phe
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 148

Ile Lys Leu Phe Pro Trp Phe Asn Gln Phe
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
```

```
<400> SEQUENCE: 149

Ile Xaa Leu Phe Pro Trp Phe Asn Gln Phe
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 150

Ile Lys Leu Phe Pro Phe Trp Asn Gln Phe
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 151

Ile Xaa Leu Phe Pro Phe Trp Asn Gln Phe
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 152

Ile Lys Leu Phe Pro Tyr Trp Asn Gln Phe
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 153

Ile Xaa Leu Phe Pro Tyr Trp Asn Gln Phe
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 154

Ile Lys Leu Phe Pro Tyr Phe Asn Gln Phe
1               5                   10
```

```
<210> SEQ ID NO 155
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 155

Ile Xaa Leu Phe Pro Tyr Phe Asn Gln Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 156

Ile Lys Leu Phe Pro Phe Tyr Asn Gln Phe
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 157

Ile Xaa Leu Phe Pro Phe Tyr Asn Gln Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 158

Ile Lys Leu Phe Pro Trp Tyr Asn Gln Phe
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 159

Ile Xaa Leu Phe Pro Trp Tyr Asn Gln Phe
1               5                   10

<210> SEQ ID NO 160
```

-continued

```
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 160

Ile Lys Leu Phe Pro Phe Phe Asn Gln Phe
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 161

Ile Xaa Leu Phe Pro Phe Phe Asn Gln Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 162

Val Lys Leu Phe Pro Leu Trp Asn Gln Phe
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 163

Val Xaa Leu Phe Pro Leu Trp Asn Gln Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 164

Val Lys Leu Phe Pro Leu Phe Asn Gln Phe
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
```

```
<221> NAME/KEY: MOD_RES
<222> LOCATION: (2)..(2)
<223> OTHER INFORMATION: Orn

<400> SEQUENCE: 165

Val Xaa Leu Phe Pro Leu Phe Asn Gln Phe
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 166

Val Lys Leu Phe Pro Leu Tyr Asn Gln Phe
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 167

Val Xaa Leu Phe Pro Leu Tyr Asn Gln Phe
1               5                   10

<210> SEQ ID NO 168
<211> LENGTH: 10
<212> TYPE: PRT
<213> ORGANISM: Aneurinibacillus migulanus
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 168

Val Xaa Leu Phe Pro Val Xaa Leu Phe Pro
1               5                   10

<210> SEQ ID NO 169
<211> LENGTH: 10
<212> TYPE: PRT
<213> ORGANISM: Aneurinibacillus migulanus
<220> FEATURE:
<221> NAME/KEY: MOD_RES
<222> LOCATION: (7)..(7)
<223> OTHER INFORMATION: Orn

<400> SEQUENCE: 169

Val Lys Leu Phe Pro Val Xaa Leu Phe Pro
1               5                   10

<210> SEQ ID NO 170
<211> LENGTH: 10
<212> TYPE: PRT
<213> ORGANISM: Aneurinibacillus migulanus
```

-continued

```
<400> SEQUENCE: 170

Val Lys Leu Phe Pro Val Lys Leu Phe Pro
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 171

Leu Xaa Leu Phe Pro Val Xaa Leu Phe Pro
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (7)..(7)
<223> OTHER INFORMATION: Orn

<400> SEQUENCE: 172

Leu Lys Leu Phe Pro Val Xaa Leu Phe Pro
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn

<400> SEQUENCE: 173

Leu Xaa Leu Phe Pro Val Lys Leu Phe Pro
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 174

Leu Lys Leu Phe Pro Val Lys Leu Phe Pro
1               5                   10

<210> SEQ ID NO 175
<211> LENGTH: 10
<212> TYPE: PRT
<213> ORGANISM: Artificial Sequence
<220> FEATURE:
```

```
<223> OTHER INFORMATION: Artificial construct; Cyclic polypeptide
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 175

Leu Xaa Leu Phe Pro Leu Xaa Leu Phe Pro
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Artificial construct; Cyclic polypeptide
<220> FEATURE:
<221> NAME/KEY: MOD_RES
<222> LOCATION: (7)..(7)
<223> OTHER INFORMATION: Orn

<400> SEQUENCE: 176

Leu Lys Leu Phe Pro Leu Xaa Leu Phe Pro
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Artificial construct; Cyclic polypeptide

<400> SEQUENCE: 177

Leu Lys Leu Phe Pro Leu Lys Leu Phe Pro
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: Orn

<400> SEQUENCE: 178

Asn Gln Tyr Val Xaa
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 179

Asn Gln Tyr Val Lys
1               5

<210> SEQ ID NO 180
<211> LENGTH: 5
<212> TYPE: PRT
```

```
<213> ORGANISM: Artificial Sequence
<220> FEATURE:
<223> OTHER INFORMATION: Synthetic Peptide

<400> SEQUENCE: 180

Leu Phe Pro Phe Phe
1               5
```